US012576274B2

(12) United States Patent
Yazdan-Shahmorad et al.

(10) Patent No.: US 12,576,274 B2
(45) Date of Patent: Mar. 17, 2026

---

(54) TREATING STROKE USING ELECTRICAL STIMULATION

(71) Applicant: University of Washington, Seattle, WA (US)

(72) Inventors: Azadeh Yazdan-Shahmorad, Seattle, WA (US); Zixuan Zhou, Seattle, WA (US); Karam Khateeb, Seattle, WA (US); Mona Rahimi, Seattle, WA (US); Aryaman Gala, Seattle, WA (US)

(73) Assignee: University of Washington, Seattle, WA (US)

( * ) Notice: Subject to any disclaimer, the term of this patent is extended or adjusted under 35 U.S.C. 154(b) by 307 days.

(21) Appl. No.: 18/219,047

(22) Filed: Jul. 6, 2023

(65) Prior Publication Data

US 2024/0009460 A1 Jan. 11, 2024

Related U.S. Application Data

(60) Provisional application No. 63/359,180, filed on Jul. 7, 2022.

(51) Int. Cl.
*A61N 1/36* (2006.01)
*A61N 1/05* (2006.01)

(52) U.S. Cl.
CPC ....... *A61N 1/36103* (2013.01); *A61N 1/0531* (2013.01); *A61N 1/36064* (2013.01); *A61N 1/36067* (2013.01); *A61N 1/36139* (2013.01)

(58) Field of Classification Search
CPC .............. A61N 1/36103; A61N 1/0531; A61N 1/36064; A61N 1/36067; A61N 1/36139
See application file for complete search history.

(56) References Cited

U.S. PATENT DOCUMENTS

| | | | |
|---|---|---|---|
| 8,958,881 B2 | 2/2015 | Lamensdorf et al. | |
| 10,537,728 B2 | 1/2020 | Simon et al. | |
| 10,688,301 B2 | 6/2020 | Solomon | |
| 2005/0021106 A1 | 1/2005 | Firlik et al. | |
| 2010/0069995 A1* | 3/2010 | Danielsson | A61N 1/36114 607/50 |
| 2017/0021161 A1 | 1/2017 | De Ridder | |

(Continued)

OTHER PUBLICATIONS

Dohmen, Christian, et al. "Spreading Depolarizations Occur in Human Ischemic Stroke with High Incidence." Annals of Neurology, vol. 63, No. 6, Jun. 2008, pp. 720-728, https://doi.org/10.1002/ana.21390 (Year: 2008).*

(Continued)

*Primary Examiner* — Paula J Stice
(74) *Attorney, Agent, or Firm* — Katherine M. Mead; Lee & Hayes, PC

(57) ABSTRACT

Techniques for treating acute ischemic stroke, and other neurological pathologies, are described herein. An example method includes identifying a portion of a brain including overactive neurons and outputting an electrical signal to at least one stimulation electrode disposed away from the portion of the brain by a distance in a range of about 0.5 mm to 1 cm. The electrical signal includes a low-frequency component including bursts having a frequency in a range of about 2 Hz to about 10 Hz. The electrical signal includes a high-frequency component comprising pulses having a frequency in a range of about 200 Hz to about 2 kHz.

20 Claims, 10 Drawing Sheets

(56) References Cited

U.S. PATENT DOCUMENTS

2019/0321639 A1* 10/2019 Rao ..................... A61N 1/0529
2020/0398057 A1* 12/2020 Esteller ............. A61N 1/36175

OTHER PUBLICATIONS

Adkins-Muir & Jones, et al., "Cortical electrical stimulation combined with rehabilitative training: Enhanced functional recovery and dendritic plasticity following focal cortical ischemia in rats," Neurological Research, vol. 25, 2003, pp. 780-788.

Baba, et al., "Electrical Stimulation of the Cerebral Cortex Exerts Antiapoptotic, Angiogenic, and Anti-Inflammatory Effects in Ischemic Stroke Rats Through Phosphoinositide 3-Kinase/Akt Signaling Pathway," Stroke, 2009, vol. 40, No. 11, pp. e598-605.

Bao, et al., "Rewiring the Lesioned Brain: Electrical Stimulation for Post-Stroke Motor Restoration," Journal of Stroke, vol. 22, No. 1, 2020, pp. 47-63.

Barros, et al., "The pattern of c-Fos expression and its refractory period in the brain of rats and monkeys," Frontiers in Cellular Neuroscience, vol. 9, No. 72, 2015, pp. 1-8.

Beurrier, et al., "High-Frequency Stimulation Produces a Transient Blockade of Voltage-Gated Currents in Subthalamic Neurons," The American Physiological Society, vol. 85, No. 4, 2001, pp. 1351-1356.

Boonzaier, et al., "Noninvasive Brain Stimulation to Enhance Functional Recovery After Stroke: Studies in Animal Models," Neurorehabilitation and Neural Repair, vol. 32, No. 11, 2018, pp. 927-940.

Brott and Bogousslavsky, "Treatment of Acute Ischemic Stroke," The New England Journal of Medicine, vol. 343, No. 10, 2000, pp. 710-722.

Buetefisch, et al., "Neuroprotection of Low-Frequency Repetitive Transcranial Magnetic Stimulation after Ischemic Stroke in Rats," Annals of Neurology, vol. 93, No. 2, 2023, pp. 336-347.

Buitrago, et al., "Effects of somatosensory electrical stimulation on neuronal injury after global hypoxia-ischemia," Experimental Brain Research, vol. 158, 2004, pp. 336-344.

Butler and Pennypacker, "Temporal and regional expression of Fos-related proteins in response to ischemic injury," Brain Research Bulletin, vol. 63, 2004, pp. 65-73.

Buzsáaki and Wang, "Mechanisms of Gamma Oscillations," Annual Review of Neuroscience, vol. 35, 2012, pp. 203-225.

Carmichael and Chesselet, "Synchronous Neuronal Activity Is a Signal for Axonal Sprouting after Cortical Lesions in the Adult," The Journal of Neuroscience, vol. 22, No. 14, 2002, pp. 6062-6070.

CDC Morbidity and Mortality Weekly Report, "Impact of the 1999 AAP/USPHS Joint Statement on Thimerosal in Vaccines on Infant Hepatitis B Vaccination Practices," JAMA, vol. 285, No. 12, 2001, pp. 1568-1572.

Chamorro, et al., "Neuroprotection in acute stroke: targeting excitotoxicity, oxidative and nitrosative stress, and inflammation," The Lancet Neurology, vol. 15, No. 8, 2016, pp. 869-881.

Cheng, et al., "Neuroprotection for Ischemic Stroke: Two Decades of Success and Failure," The American Society for Experimental Neuro Therapeutics, Inc., vol. 1, 2004, pp. 36-45.

Cogan, et al., "Tissue damage thresholds during therapeutic electrical stimulation," Journal of Neural Engineering, vol. 13, No. 2, 2016, pp. 1-26.

Cook and Tymianski, "Nonhuman Primate Models of Stroke for Translational Neuroprotection Research," Neurotherapeutics, vol. 9, No. 2, 2012, pp. 371-379.

Coscia, et al., "Neurotechnology-aided interventions for upper limb motor rehabilitation in severe chronic stroke," Brain, vol. 142, 2019, pp. 2182-2197.

Danton and Dietrich, "The Search for Neuroprotective Strategies in Stroke," American Journal of Neuroradiology, vol. 25, No. 2, 2004, pp. 181-194.

Dohmen, et al., "Spreading Depolarizations Occur in Human Ischemic Stroke with High Incidence," Annals of Neurology, vol. 63, No. 6, 2008, pp. 720-728.

Dreier, "The role of spreading depression, spreading depolarization and spreading ischemia in neurological disease," Nature Medicine, vol. 17, No. 4, 2011, pp. 439-447.

Edwardson, "New modalities of brain stimulation for stroke rehabilitation," Experimental Brain Research, vol. 224, No. 3, 2013, pp. 335-358.

Elias, et al., "Deep brain stimulation for stroke: Current uses and future directions," Brain Stimulation, vol. 11, 2018, pp. 3-28.

Fan, et al., "Nonhuman primate models of focal cerebral ischemia," Neural Regeneration Research, vol. 12, No. 2, 2017, pp. 321-328.

Feigin, "Global, regional, and national burden of stroke and its risk factors, 1990-2019: a systematic analysis for the Global Burden of Disease Study 2019," The Lancet Neurology, vol. 20, No. 10, pp. 795-820.

Feigin, et al., "Global and regional burden of stroke during 1990-2010: findings from the Global Burden of Disease Study 2010," Lancet, vol. 383, No. 9913, 2014, pp. 245-254.

Ginsberg, "Neuroprotection for Ischemic Stroke: Past, Present and Future," Neuropharmacology, vol. 55, No. 3, 2008, pp. 363-389.

Griggs, et al., "Multi-modal artificial dura for simultaneous large-scale optical access and large-scale electrophysiology in non-human primate cortex," Journal of Neural Engineering, vol. 18, No. 5, 2021, pp. 1-21.

Griggs, et al., "Optimized large-scale optogenetic interface for non-human primates," Optogenetics and Optical Manipulation, vol. 1086605, 2019, 10 pages.

Hermann, et al., "Relationship Between Metabolic Dysfunctions, Gene Responses and Delayed Cell Death After Mild Focal Cerebral Ischemia in Mice," Neuroscience, vol. 104, No. 4, 2001, pp. 947-955.

Herrera and Robertson, "Activation of c-fos in the brain," Progress in Neurobiology, vol. 50, 1996, pp. 83-107.

Hosseini, et al., "Central Nervous System Electrical Stimulation for Neuroprotection in Acute Cerebral Ischemia: Meta-Analysis of Preclinical Studies," Stroke, vol. 50, No. 10, 2019, pp. 2892-2901.

Huang, et al., "The theoretical model of theta burst form of repetitive transcranial magnetic stimulation," Clinical Neurophysiology, vol. 122, No. 5, 2011, pp. 1011-1018.

Huang, et al., "Theta Burst Stimulation of the Human Motor Cortex," Neuron, vol. 45, No. 2, 2005, pp. 201-206.

Jurga, et al., "Overview of General and Discriminating Markers of Differential Microglia Phenotypes," Frontiers in Cellular Neuroscience, vol. 14, No. 198, 2020, pp. 1-18.

Khanna, et al., "Low-frequency stimulation enhances ensemble co-firing and dexterity after stroke," Cell, vol. 184, No. 4, 2021, pp. 912-930.

Khateeb, et al., "A Practical Method for Creating Targeted Focal Ischemic Stroke in the Cortex of Nonhuman Primates," 41st Annual International Conference of the IEEE Engineering in Medicine and Biology Society, 2019, pp. 3515-3518.

Khateeb, et al., "A toolbox for studying cortical physiology in primates," bioRxiv, 2021, pp. 1-50.

Khateeb, et al., "A versatile toolbox for studying cortical physiology in primates," Cell Reports Methods, vol. 2, No. 3, 2022, 19 pages.

Khedr, et al., "Therapeutic trial of repetitive transcranial magnetic stimulation after acute ischemic stroke," Neurology, vol. 65, No. 3, 2005, pp. 466-468.

Kirdajova, et al., "Ischemia-Triggered Glutamate Excitotoxicity From the Perspective of Glial Cells," Frontiers in Cellular Neuroscience, vol. 14, No. 51, 2020, pp. 1-27.

Kleim, et al., "Motor cortex stimulation enhances motor recovery and reduces peri-infarct dysfunction following ischemic insult," Neurological Research, vol. 25, 2003, pp. 789-793.

Knecht, et al., "Adjunctive Therapy Approaches for Ischemic Stroke: Innovations to Expand Time Window of Treatment," International Journal of Molecular Sciences, vol. 18, No. 12, 2017, pp. 1-18.

Labat-gest and Tomasi, "Photothrombotic Ischemia: A Minimally Invasive and Reproducible Photochemical Cortical Lesion Model for Mouse Stroke Studies," Journal of Visualized Experiments, vol. 76, 2013, pp. 1-6.

(56)          References Cited

OTHER PUBLICATIONS

Lay, et al., "Mild Sensory Stimulation Completely Protects the Adult Rodent Cortex from Ischemic Stroke," Plos One, vol. 5, No. 6, 2010, pp. 1-16.

Levy, et al., "Epidural Electrical Stimulation for Stroke Rehabilitation: Results of the Prospective, Multicenter, Randomized, Single-Blinded Everest Trial," Neurorehabilitation and Neural Repair, vol. 30, No. 2, 2016, pp. 107-119.

Notturno, et a., "Neuroprotective effect of cathodal transcranial direct current stimulation in a rat stroke model," Journal of the Neurological Sciences, vol. 342, 2014, pp. 146-151.

Paxinos, et al., "The Rhesus Monkey Brain in Stereotaxic Coordinates," Academic Press, 1999, pp. 1-2.

Peruzzotti-Jametti, et al., "Safety and Efficacy of Transcranial Direct Current Stimulation in Acute Experimental Ischemic Stroke," Stroke, vol. 44, No. 11, 2013, pp. 3166-3174.

Popovic, et al., "Electrical stimulation as a means for achieving recovery of function in stroke patients," NeuroRehabilitation, vol. 25, No. 1, 2009, pp. 45-58.

Prabhakaran, et al., "Acute Stroke Intervention: A Systematic Review," The Journal of the American Medical Association, vol. 313, No. 14, 2015, pp. 1451-1462.

Rebesco and Miller, "Enhanced detection threshold for in vivo cortical stimulation produced by Hebbian conditioning," Journal of Neural Engineering, vol. 8, No. 1, 2011, pp. 1-21.

Schlaug and Renga, "Transcranial direct current stimulation: a noninvasive tool to facilitate stroke recovery," Expert Review of Medical Devices, vol. 5, No. 6, 2008, pp. 759-768.

Shi, et al., "A new era for stroke therapy: Integrating neurovascular protection with optimal reperfusion," Journal of Cerebral Blood Flow & Metabolism, vol. 38, No. 12, 2018, pp. 2073-2091.

Shreve, et al., "Electroencephalography measures are useful for identifying large acute ischemic stroke in the Emergency Department," Journal of Stroke and Cerebrovascular Diseases, vol. 28, No. 8, 2019, pp. 1-14.

Sommer, "Ischemic stroke: experimental models and reality," Acta Neuropathologica, vol. 133, 2017, pp. 245-261.

Stagg, et al., "Neurochemical Effects of Theta Burst Stimulation as Assessed by Magnetic Resonance Spectroscopy," Journal of Neurophysiology, vol. 101, No. 6, 2009, pp. 2872-2877.

Stinear, et al., "Advances and challenges in stroke rehabilitation," The Lancet Neurology, vol. 19, No. 4, 2020, pp. 348-360.

Teskey, et al., "Cortical stimulation improves skilled forelimb use following a focal ischemic infarct in the rat," Neurological Research, vol. 25, 2003, pp. 794-800.

Tsao, et al., "Heart Disease and Stroke Statistic-2022 Update: A Report From the American Heart Association," Circulation, vol. 145, No. 8, 2022, pp. e153-639.

Uemura, et al., "Focal ischemia in rats causes time-dependent expression of c-fos protein immunoreactivity in widespread regions of ipsilateral cortex," Brain Research, vol. 552, No. 1, 1991, pp. 99-105.

Von Bornstädt, et al., "Supply-demand mismatch transients in susceptible peri-infarct hot zones explain the origin of spreading injury depolarizations," Neuron, vol. 85, No. 5, 2015, pp. 1117-1131.

Wang, et al., "Somatosensory Cortical Electrical Stimulation After Reperfusion Attenuates Ischemia/Reperfusion Injury of Rat Brain," Frontiers in Aging Neuroscience, vol. 13, No. 741168, 2021, pp. 1-12.

Wann, et al., "Rapid development of strong, persistent, spatiotemporally extensive cortical synchrony and underlying oscillations following acute MCA focal ischemia," Scientific Reports, vol. 10, No. 21441, 2020, pp. 1-14.

Woitzik, et al., "Propagation of cortical spreading depolarization in the human cortex after malignant stroke," American Academy of Neurology, vol. 80, No. 12, 2013, pp. 1095-1102.

Yazdan-Shahmorad, et al. "Polarity of cortical electrical stimulation differentially affects neuronal activity of deep and superficial layers of rat motor cortex," Brain Stimulation, vol. 4. No. 4, 2011, pp. 228-241.

Yazdan-Shahmorad, et al., "High gamma power in ECoG reflects cortical electrical stimulation effects on unit activity in layers V/VI," Journal of Neural Engineering, vol. 10, No. 6, 2013, pp. 1-24.

Yazdan-Shahmorad, et al., "Targeted cortical reorganization using optogenetics in non-human primates," eLife, 2018, pp. 1-21.

* cited by examiner

LOW-
FREQUENCY
COMPONENT
402

HIGH-
FREQUENCY
COMPONENT
404

$f_b$ $f_p$

*Frequency*

2 Hz          10 Hz          200 Hz          2 kHz

BURST
DURATION
406

BURST
PERIOD
408

*Time*

PULSE
PERIOD
412

PAUSE
DURATION
410

500

600

DEVICE(S) 700

MEMORY 704

COMPONENT(S) 718

SIGNAL GENERATOR 118

MONITORING CIRCUIT 122

ANALYSIS SYSTEM 124

PROCESSOR(S) 706

REMOVABLE STORAGE 708

NON-REMOVABLE STORAGE 710

INPUT DEVICE(S) 712

OUTPUT DEVICE(S) 714

TRANSCEIVER(S) 716

TREATING STROKE USING ELECTRICAL STIMULATION

CROSS-REFERENCE TO RELATED APPLICATION

This application claims the priority of U.S. Provisional App. No. 63/359,180, filed on Jul. 7, 2022, which is incorporated by reference herein in its entirety.

STATEMENT REGARDING FEDERALLY SPONSORED RESEARCH OR DEVELOPMENT

This invention was made with government support under Grant Nos. 1R01NS119395-01 and P51 OD010425, awarded by the National Institutes of Health and Grant No. EEC-1028725, awarded by the National Science Foundation. The government has certain rights in the invention.

BACKGROUND

Ischemic stroke is a major type of brain injury that results in high mortality and serious long-term disability for adults, especially in the aging population. Globally, over 7.6 million people suffer from ischemic stroke each year, causing significant health and economic burdens worldwide. An ischemic stroke happens when blood flow within the brain is interrupted, leading to a lack of oxygen supply, energy depletion, and subsequent neuronal death. Acute intervention within hours (e.g., within 24 hours) after stroke onset offers the most critical therapeutic opportunity as it can reduce irreversible tissue injury and resulting in improved neurological and functional outcome for stroke patients (S. Prabhakaran, et al., JAMA, vol. 313, no. 14, pp. 1451-62, April 2015). However, currently available treatments within the acute window are highly limited, and approved interventions such as the administration of tissue plasminogen activator (t-PA) and catheter-based thrombectomy, often have strict patient selection criteria (T. Brott and J. Bogousslaysky, N. Engl. J. Med., vol. 343, no. 10, pp. 710-22, September 2000). During the past few decades, there has been a large amount of experimental research and clinical trials on neuroprotective drug treatments for acute ischemic stroke, with the aim to interrupt the ischemic cascades and thereby reduce neuronal death (Y. D. Cheng, et a., "Neuroprotection for ischemic stroke: Two decades of success and failure," vol. 1, no. 1, p. 10, 2004; Chamorro, et al., Lancet Neurol., vol. 15, no. 8, pp. 869-81, July 2016; Danton and Dietrich, "Am. J. Neuroradiol., vol. 25, no. 2, pp. 181-194, February 2004). However, most of the drug trials failed to show consistent clinical efficacy when moving from animals to human (M. D. Ginsberg, Neuropharmacology, vol. 55, no. 3, pp. 363-89, September 2008; Cook and Tymianski, Expert Rev. Cardiovasc. Ther., vol. 9, no. 4, pp. 433-449, April 2011; L. Shi et al., J. Cereb. Blood Flow Metab., vol. 38, no. 12, pp. 2073-91, December 2018). Therefore, there is a pressing need to expand the therapeutic options for acute ischemic stroke and improve the translation from bench to bedside to help millions of stroke patients retain the maximum quality of life.

In recent years, novel neural modulation paradigms such as electrical brain stimulation have been proposed as a promising treatment for ischemic stroke. Most of these stimulation paradigms target the subacute or chronic phase of stroke (e.g., after the acute phase) to promote neural plasticity and functional recovery, rather than reducing permanent ischemic damage (Adkins-Muir and Jones, Neurol.

Res., vol. 25, no. 8, pp. 780-788, December 2003; Kleim, et al., Neurol. Res., vol. 25, no. 8, pp. 789-93, December 2003; P. Khanna, D. Totten, L. Novik, J. Roberts, R. J. Morecraft, and K. Ganguly, "Low-frequency stimulation enhances ensemble co-firing and dexterity after stroke," Cell, vol. 184, no. 4, pp. 912-930.e20, February 2021, doi: 10.1016/j.cell.2021.01.023; Boonzaier et al., Neurorehabil. Neural Repair, vol. 32, no. 11, pp. 927-940, November 2018; Popović et al., NeuroRehabilitation, vol. 25, pp. 45-58, February 2009; Bao et al., J. Stroke, vol. 22, no. 1, pp. 47-63, January 2020). As a result, it might take months of treatment in conjunction with rehabilitative training for only a subset of patients to see positive results from these interventions (Levy et al., Neurorehabil. Neural Repair, vol. 30, no. 2, pp. 107-119, February 2016; Coscia et al., Brain, vol. 142, no. 8, pp. 2182-2197, August 2019; Stinear et al., Lancet Neurol., vol. 19, no. 4, pp. 348-360, April 2020).

Previously, electrical stimulation during the acute phase was presumed to cause further adverse effects to individuals with ischemic stroke, causing greater tissue damage related to ischemia-induced electrical instability and spreading depolarizations (SDs). It has been widely reported that perilesional tissues are particularly susceptible to SDs, marked by intense neuronal depolarization waves that can lead to increased metabolic stress, neuronal swelling, and lesion progression (Dohmen et al., Ann. Neurol., vol. 63, no. 6, pp. 720-728, 2008; Woitzik et al., Neurology, vol. 80, no. 12, pp. 1095-1102, March 2013; Dreier, Nat. Med., vol. 17, no. 4, Art. no. 4, April 2011; von Bornstädt et al., Neuron, vol. 85, no. 5, pp. 1117-1131, March 2015).

DETAILED DESCRIPTION

Various implementations described herein relate to techniques, systems, apparatuses, and methods for treating a neurological disease using electrical stimulation. In some examples, the neurological disease is ischemic stroke. For instance, electrical stimulation described herein can calm overactive neurons in the brain in the acute phase following ischemic stroke (e.g., within 24 hours after an ischemic stroke occurs or otherwise begins), thereby preserving neuronal tissue and neuroplasticity.

In various examples, the frequency- and time-domain characteristics of the electrical signal are optimized to reduce overactivity in neurons without causing additional damage to the neurons. In various cases, the electrical signal is administered in one or more blocks, which occur continuously on an order of minutes. Within each block, the electrical signal includes low-frequency bursts carrying high-frequency pulses. The electrical signal is charge-balanced during administration to the target neuronal tissue. Implementations described herein include both invasive and noninvasive techniques.

Various implementations of the present disclosure are directed to improvements in the technological field of neurological treatments, such as treatments for ischemic stroke. Many previous treatments for ischemic stroke were designed to be administered after the acute phase, such as over 24 hours after an ischemic stroke is initiated. Thus, these treatments cannot prevent neuronal death and other damage that occurs during the acute phase. Some treatments, involving invasive procedures and pharmaceutical therapies, can be administered during the acute phase, but have various drawbacks. In implementations of the present disclosure, minimally invasive electrical stimulation provides a promising treatment for reducing neuronal hyperactivity during the acute phase of ischemic stroke, thereby preventing widespread neuronal death in the brain due to the ischemic stroke.

Implementations of the present disclosure will now be described with reference to the accompanying drawings.

Figure 1:
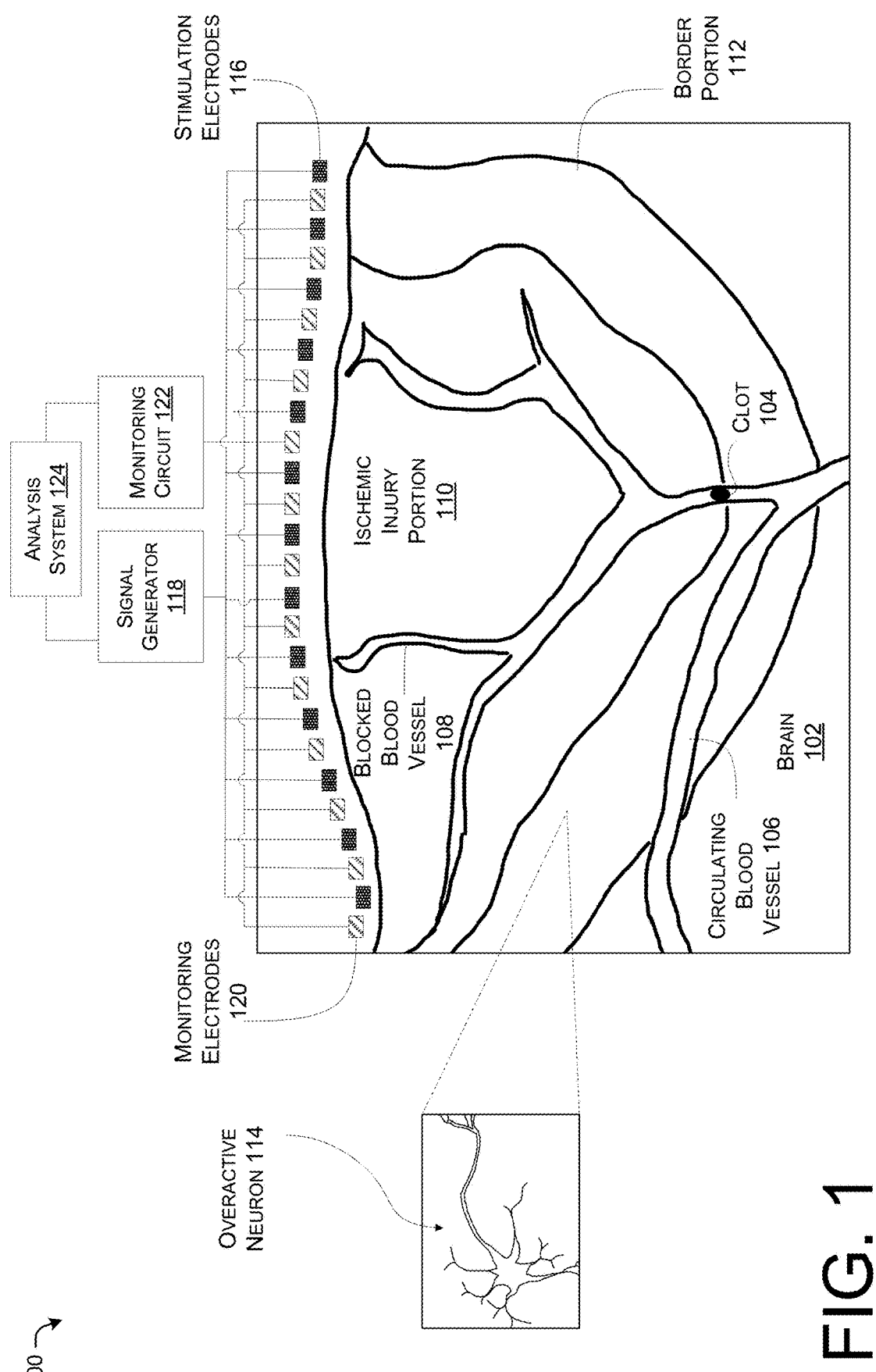
FIG. 1 illustrates an example environment for treating neuronal hyperactivity using electrical stimulation.

FIG. 1 illustrates an example environment 100 for treating neuronal hyperactivity using electrical stimulation. The environment 100 depicts a portion of a brain 102 of a subject. In various cases, the subject is a human. For example, the human may be a patient presenting to a clinical environment, such as a hospital, with symptoms associated with an acute phase of ischemic stroke. In various cases, the subject is within a predetermined time period (e.g., 24 hours, 12 hours, 8 hours, 4 hours, 1 hour, or the like) of suffering from an ischemic stroke. In some cases, the subject is a non-human subject, such as a non-human primate (NHP) or other type of non-human animal.

Physiologically, neurons in the brain 102 are supplied with blood via a network of blood vessels. FIG. 1 illustrates an example cross-section of the brain 102, but it may be understood that tissue in the brain 102 containing the neurons, and the network of blood vessels, exist in three dimensions (3D). In various implementations, blood is configured to travel through a circulating blood vessel 106 in the brain 102. However, a clot 104 is present that at least partially obstructs blood flow through a blocked blood vessel 108. The clot 104, for instance, causes the ischemic stroke suffered by the subject.

Due to the presence of the clot 104, an ischemic injury portion 110 of the brain 102 is generated. The blood supply for the ischemic injury portion 110 includes the blocked blood vessel 108. Therefore, neurons in the ischemic injury portion 110 are prevented from receiving sufficient oxygen due to the presence of the clot 104. As a result, the neurons in the ischemic injury portion 110 may die from hypoxia.

In various cases, the blocked blood vessel 108 also partially supplies a border portion 112 of the brain 102. However, the border portion 112, in various cases, may also receive at least some oxygen from the circulating blood vessel 106 and/or additional blood vessels (not pictured in the cross-section illustrated in FIG. 1) that may supply oxygenated blood to the brain 102 despite the clot 104.

According to some examples, the border portion 112 includes neurons that are receiving some oxygenation from the cardiovascular system of the subject. However, they may receive a low amount of oxygen compared to a state in which the clot 104 is not present. Thus, the neurons in the border portion 112 may experience physiological stress that causes the neurons to become overactive. As used herein, the terms "overactive," "hyperactive," and their equivalents, may refer to neurons engaging in action potentials at a frequency that is greater than 30 Hz. For example, neurons that are overactive may have significantly elevated action potential firing rates compared to non-overactive, healthy brain regions. In various cases, overactivity can be detected by measuring an electrical signal from a group of neurons over time, wherein an amplitude of a frequency component of the electrical signal defined in a range between 30 Hz and 400 Hz is above a predetermined threshold. For example, the border portion 112 may include overactive neuron 114.

The overactivity of the neurons in the border portion 112 may increase the oxygen demand of the neurons. However, the oxygen supply to the neurons may be limited due to the presence of the clot 104. As a result of the reduced oxygen supply (due to the clot 104) and the heightened oxygen demand of the neurons (due to overactivity), the neurons within the border portion 112 may become damaged. Without acute treatment, the neurons in the border portion 112 may die, which can lead to extensive and irreversible damage to the brain 102. For instance, the overactive neuron 114 in the border portion 112 may die if left untreated for more than a threshold time period (e.g., 24 hours) after the clot 104 is formed.

In various implementations of the present disclosure, the neurons in the border portion 112 are treated using an electrical signal (also referred to as a "treatment signal"). The electrical signal, in various cases, reduces an activity of the neurons in the border portion 112, and may thereby reduce the oxygen demands of the neurons in the border portion 112. In other words, the electrical signal may "calm" down the neurons within the border portion 112. Thus, the neurons in the border portion 112 are more likely to survive by the time the clot 104 is removed or otherwise treated, and blood perfusion returns to the blocked blood vessel 108. In some examples, the clot 104 cannot be removed. The electrical signal may help preserve neurons in these examples until there are increases in collateral blood flow and/or new blood vessels are formed that provide additional blood supply to the neurons being treated.

An array of stimulation electrodes 116 is disposed proximate to the border portion 112. In some cases, the stimulation electrodes 116 include invasive electrodes, such as electrocorticography (ECoG) electrodes. For instance, the stimulation electrodes 116 may be disposed on a surface of the brain 102. In some examples, the stimulation electrodes 116 include noninvasive electrodes, such as transcranial electrodes. For instance, the stimulation electrodes 116 may be disposed on a skull of the subject. In various cases, the stimulation electrodes 116 are disposed within a threshold distance of the border portion 112 of the brain 102. For example, at least one of the stimulation electrodes 116 is disposed within 1 centimeter (cm) of at least a section of the border portion 112.

A signal generator 118 is coupled to the stimulation electrodes 116. In various implementations, the signal generator 118 outputs the electrical signal to at least one of the stimulation electrodes 116. For example, the signal generator 118 outputs an electrical signal between at least one of the stimulation electrodes 116 and a reference electrode (not illustrated), which may be disposed on a portion of the body of the subject. The reference or ground electrode, for instance, is positioned such that the electrical signal is output to at least a portion of the border portion 112 of the brain 102. In various cases, the electrical signal can be represented as a voltage between the at least one stimulation electrode 116 and the reference or ground electrode. In some examples, the electrical signal can be represented as a current induced in at least a portion of the border portion 112 of the brain 102.

In some implementations, the signal generator 118 is configured to selectively output the electrical signal to at least one of the stimulation electrodes 116, and refrain from outputting the electrical signal to at least one of the stimulation electrodes 116. For instance, the signal generator 118 may include one or more switches that are configured to selectively disconnect one or more of the stimulation electrodes 116 from a portion of the signal generator 118 configured to output the electrical signal. The signal generator 118, for instance, may include at least one of a voltage supply (e.g., at least one capacitor and/or battery, a plug configured to connect the signal generator 118 to mains power, etc.), a current supply, one or more resistors, one or more potentiometers, one or more capacitors, one or more inductors, one or more transistors, one or more transformers, or any other analog circuit element that enables the signal generator 118 to output the electrical signal described herein.

In various cases, the signal generator 118 varies a magnitude (e.g., an amplitude) of the electrical signal over time. The electrical signal with respect to time, for instance, may vary as at least one periodic waveform, such as a sinusoidal waveform, a square wave, a pulse wave, a triangle wave, a sawtooth wave, or any combination thereof. In various implementations, the electrical signal is charge balanced. As used herein, the term "charge balanced," and its equivalents, may refer to a characteristic of an electrical signal that, when applied to an object, does not induce electric charging (e.g., an increase or decrease in an electrostatic charge) of the object over time. In various examples, a charge balanced electrical signal has the same amount of charge in an anodal phase and a cathodal phase, such that it does not induce electric charging. For instance, a sinusoidal current waveform is charged balanced when it is centered at a 0 Amperes (A). The charge balance of the electrical signal may prevent degradation of the stimulation electrodes 116. In various cases, the charge balance of the electrical signal prevents damage to the neurons in the brain 102.

The electrical signal may include multiple components defined at multiple frequency ranges. In various implementations, the electrical signal includes pulses characterized at a relatively high frequency range. According to some implementations, the pulses include at least one frequency in a range of 200 Hz to 4 kilohertz (kHz), such as in a range of 200 Hz to 4 kHz or 500 Hz to 4 kHz. For instance, a waveform representing the pulses over time may have the shape of a periodic square wave that is centered at a magnitude of 0 and has a primary frequency in a range of 200 Hz to 4 kHz.

In various cases, the electrical signal outputs the pulses in bursts that are characterized by a relatively low frequency range. In some examples, the bursts include at least one frequency in a range of 2 Hz to 10 Hz. In various instances, the electrical signal has a magnitude of 0 between the bursts. That is, the electrical signal may be inactive between the bursts.

In some implementations, the electrical signal includes one or more blocks, during which the bursts of the pulses are defined. In various cases, each block extends for a predetermined time period. For instance, an example block has a length in a range of 10 minutes to 30 minutes. In some cases, between the blocks, the electrical signal has a magnitude of 0. That is, the electrical signal may be inactive between the blocks.

The electrical signal, for instance, omits frequencies associated with brain activation. For example, the electrical signal may omit any frequency in a range of 10 to 50 Hz.

According to various implementations, the electrical signal may have an amplitude, energy, or power level within a predetermined range. The electrical signal may have an amplitude that prevents significant heating of the brain 102 during administration of the pulses, bursts, and/or blocks. For example, a single block may have a negligible temperature impact on the brain 102 (e.g., the block may result in heating of less than 1 degree Celsius of one or more neurons in the brain 102). The amplitude, for instance, may be such that the pulse width of the electrical signal, and the size of the stimulation electrodes 116, induces a charge density in the brain 102 that is lower than a threshold associated with tissue damage. According to some examples in which the electrical signal is defined as a current, the amplitude of the electrical signal may be in a range of micro Amperes (μA) to 1 milliamperes (mA). For example, the electrical signal may have an amplitude in a range of 50 μA to 500 μA.

While the electrical signal is active, the electrical signal may lower an activity of the neurons in the border portion 112. That is, the electrical signal may reduce a metabolic and bioenergetic demand of the neurons in the border portion 112. In various cases, the electrical signal may lower the activity of the neurons in the border portion 112 after the electrical signal is active, such as minutes after the electrical signal is active. For instance, the electrical signal may reduce an action potential rate of the neurons in the border portion 112, which in turn reduces a rate of adenosine triphosphate (ATP) production in mitochondria in the neurons of the border portion 112, thereby lowering a rate of oxygen metabolized by the neurons in the border portion 112. Due to the lowered rate of oxygen metabolism, the neurons in the border portion 112 are more likely to survive while relying on the limited blood circulation of the circulating blood vessel 106 and without relying on oxygen from the blocked blood vessel 108. The electrical signal may be administered to the border portion 112 while blocked blood vessel 108 has limited to no perfusion. For instance, the electrical signal may be administered until the clot 104 is removed.

In various cases, a treatment including administration of the electrical signal can be optimized based on feedback from the brain 102. For instance, an array of monitoring electrodes 120 is configured to receive at least one electrical signal output by neurons in the brain 102 (also referred to as a "diagnostic signal"), such as by the overactive neuron 114. In some cases, the monitoring electrodes 120 include invasive electrodes, such as ECoG electrodes disposed on a surface of the brain 102. In some examples, the monitoring electrodes 120 include non-invasive electrodes, such as electroencephalography (EEG) electrodes disposed on a scalp of the subject, such that a skull of the subject is disposed between the monitoring electrodes 120 and the brain 102. Although FIG. 1 illustrates that the monitoring electrodes 120 are different than the stimulation electrodes 116, implementations are not so limited. For example, at least one of the monitoring electrodes 120 may function as at least one of the stimulation electrodes 116, or vice versa.

The neurons in the brain 102, for instance, signal to one another by participating in action potentials. For instance, a cell membrane of an example neuron maintains a baseline voltage (also referred to as a "resting state") with respect to an interior space of the neuron and an external space. During an action potential, the voltage across the membrane (also referred to as a membrane potential) may suddenly increase from the baseline (a process referred to as "depolarization"), and rapidly decrease below the baseline (a process referred to as "repolarization"), before settling back to the baseline. The action potential, for instance, is initiated when the voltage across the membrane is increased above a threshold, wherein the increase in the voltage across the membrane may be induced by an action potential performed by a neighboring neuron. Thus, the action potential is a mechanism for cell-to-cell signaling within the brain 102.

According to some implementations, an electrical signal representing the voltage changes induced by a group of neurons in the brain 102 engaging in action potentials can be received by one or more of the monitoring electrodes 120. A monitoring circuit 122 is coupled to the monitoring electrodes 120 and is configured to detect the electrical signal received by one or more of the monitoring electrodes 120. In some cases, the monitoring circuit 122 includes one or more switches (e.g., transistors) configured to selectively connect at least one of the monitoring electrodes 120 to a portion of the monitoring circuit 122 configured to detect the electrical signal, and one or more switches configured to selectively disconnect at least one of the monitoring electrodes 120 to the portion of the monitoring circuit 122. In various examples, the monitoring circuit 122 includes at least one analog-to-digital converter (ADC) configure to generate a digital signal indicative of the electrical signal received by one or more of the monitoring electrodes 120. The monitoring circuit 122, in some cases, includes analog circuit elements configured to filter the electrical signal and/or the digital signal.

According to various cases, the monitoring circuit 122 detects the electrical signal from the neurons in the brain 102 while the electrical signal administered by the stimulation electrodes 116 is inactive. The monitoring circuit 122 may detect the electrical signal from the neurons when a magnitude of the electrical signal output by the monitoring electrodes 120 is substantially equal to 0. For instance, the monitoring circuit 122 detects the electrical signal from the neurons in the brain 102 between bursts and/or blocks of the electrical signal administered by the stimulation electrodes 116.

An analysis system 124 is configured to analyze the electrical signal received by one or more of the monitoring electrodes 120 from the neurons in the brain 102. For example, the analysis system 124 may be implemented by one or more processors, which may be configured to receive the digital signal from the ADC(s) in the monitoring circuit 120, to process the digital signal, to determine a characteristic of the electrical signal received by the one or more monitoring electrodes 120, to output a signal to the signal generator 118, or any combination thereof.

In some cases, the analysis system 124 is configured to receive data indicative of other types of diagnostic information of the brain 102. For instance, the analysis system 124 may receive data indicative of a medical image of the brain (e.g., a magnetic resonance imaging (MRI) image, a functional MRI (fMRI) image, a computed tomography (CT) scan, or the like). The analysis system 124, in some cases, analyzes the data in order to determine or infer the presence and location of the overactive neurons in the border portion 112. For instance, the analysis system 124 may identify the location of the clot 102, the circulating blood vessel 106, the blocked blood vessel 108, or any combination thereof, based on the data. The analysis system 124, in some cases, determines the location of the border portion 112 based on the location of the clot 104, the location of the circulating blood vessel 106, the location of the blocked blood vessel 108, or any combination thereof.

In some implementations, the analysis system 124 is configured to identify the presence of overactive neurons in the border portion 112 based on at least one the electrical signal received by the monitoring electrodes 120 and detected by the monitoring circuit 122. For instance, the analysis system 124 may determine that at least one monitoring electrode 120 has received an electrical signal from a group of neurons in the brain 102 that indicates that the group is overactivated. In various cases, overactive neurons emit an electrical signal with a relatively high magnitude of a frequency component that is within a range of 30 Hz to 300 Hz. Thus, the analysis system 124 may identify the presence of the overactive neurons by converting the data indicative of the electrical signal to the frequency domain (e.g., by performing a fast Fourier transform (FFT) or other transform indicative of the frequency domain) and determining that a magnitude of a portion of the frequency domain data corresponding to at least one frequency in the range is greater than a threshold. In various cases, the analysis system 124 is configured to cause the signal generator 118 to output an electrical signal to at least one of the stimulation electrodes 116 in response to detecting the overactive neurons in the brain 102.

According to some cases, the analysis system 124 is configured to identify a location of overactive neurons in the brain 102 based on an electrical signal received from at least one of the monitoring electrodes 120. For instance, the analysis system 124 may identify a location of at least a portion of the border portion 112 by analyzing the electrical signal output by the overactive neurons in the border portion 112. In a particular example, the analysis system 124 determines that a first electrical signal detected by a first monitoring electrode among the monitoring electrodes 120 is indicative of overactive neurons. The analysis system 124 may further determine that a second electrical signal detected by a second monitoring electrode among the monitoring electrodes 120 is not indicative of overactive neurons. Therefore, the analysis system 124 may determine that the first monitoring electrode is within a threshold distance of the overactive neurons in the border portion 112. The analysis system 124 may further infer that the second monitoring electrode is not within a threshold distance of the overactive neurons in the border portion 112. If the array of the monitoring electrodes 120 is sufficiently dense, the analysis system 124 may be able to pinpoint the location of the overactive neurons in the border portion 112. In various implementations, the analysis system 124 causes the signal generator 118 to selectively output an electrical signal to one or more of the stimulation electrodes 116 that are within a threshold distance of the location of the overactive neurons in the border portion 112. For instance, the analysis system 124 may cause the signal generator 118 to selectively activate stimulation electrodes 116 that are adjacent to, or within a threshold distance of, the one or more monitoring electrodes 120 that detected an electrical signal indicative of the overactive neurons in the border portion 118.

In various implementations, the analysis system 124 can enhance the treatment administered by the signal generator 118 using feedback from the monitoring circuit 122. In some implementations, the analysis system 124 may at least temporarily pause the treatment to at least a portion of the border portion 112, in response to determining that the neurons in that portion are no longer overactive. In some cases, the analysis system 124 may increase a portion of the brain 102 that is subjected to the treatment from the stimulation electrodes 116 in response to determining that a portion of the brain 102 contains neurons that become overactivated subsequent to an initial treatment. In various cases, the analysis system 124 may cause the signal generator 118 to change at least one parameter of the electrical signal output to the monitoring electrodes 120 based on the electrical signal detected from the neurons in the brain 102. For example, the analysis system 124 may cause the signal generator 118 to change at least one of a shape of a current waveform, a shape of a voltage waveform, a current amplitude, a voltage amplitude, a frequency of the pulses, a width of the pulses, a frequency of the bursts, a width of the bursts, a length of a pause between the bursts, a length of a pause between blocks, or a time at which the electrical signal is output to the stimulation electrodes 116. Thus, the analysis system 124 may fine-tune the signal output by the stimulation electrodes 116 in order to maximize a desired effect (e.g., deactivation of the overactivated neurons in the brain 102) using a feedback loop.

According to various implementations, the stimulation electrodes 116 and/or the monitoring electrodes 120 can be incorporated into a single device that can be applied to a subject including the brain 102. For example, the stimulation electrodes 116 and/or the monitoring electrodes 120 may be disposed on or in a flexible substrate (e.g., a silicone-based substrate) that can conform to a surface of the brain 102, a skull, or a scalp. In some implementations, the flexible substrate can be affixed to the scalp of the subject, such as by a headband, skullcap, hat, or the like. Accordingly, in some cases, a single device design including the stimulation electrodes 116 and/or the monitoring electrodes 120 can be applied to a subject presenting at a care facility (e.g., a hospital) with symptoms of a neurological condition, such as ischemic stroke.

Figure 2:
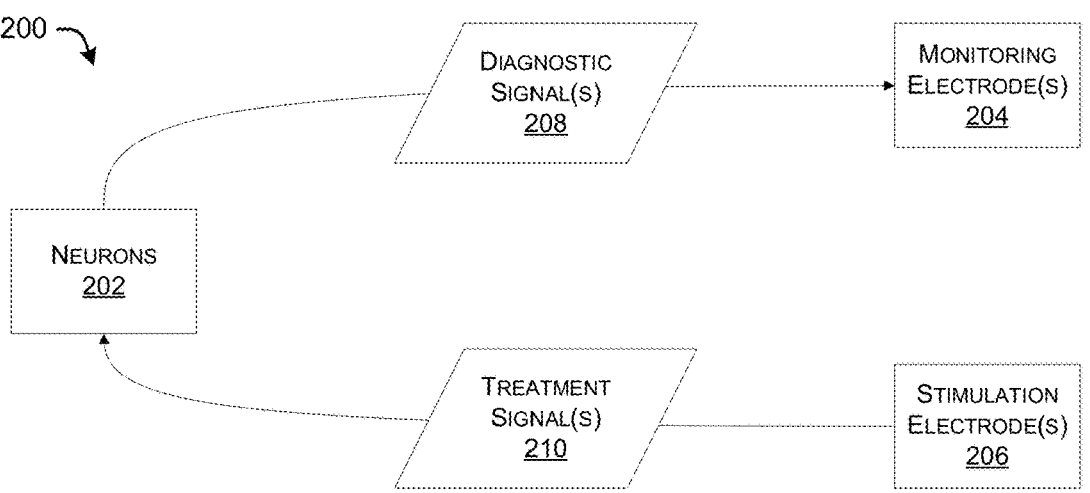
FIG. 2 illustrates example signaling for identifying and treating neuronal hyperactivity.

FIG. 2 illustrates example signaling 200 for identifying and treating neuronal hyperactivity. The signaling 200 is between neurons 202, one or more monitoring electrodes 204, and one or more stimulation electrodes 206. For instance, the neurons 202 may be located in a brain, such as the brain 102 described above with reference to FIG. 1. In some cases, the monitoring electrode(s) 204 correspond to the monitoring electrodes 120 described above with reference to FIG. 1, and the stimulation electrode(s) 206 correspond to the stimulation electrodes 116 described above with reference to FIG. 1.

In various implementations, the neurons 202 output one or more diagnostic signals 208 to the monitoring electrode(s) 204. In various cases, the diagnostic signal(s) 208 include at least one electrical signal, which can be characterized by a voltage and/or a current detected between the monitoring electrode(s) 204 and a reference electrode. In some examples, the neurons 202 engage in action potentials that generate the diagnostic signal(s) 208. For instance, a group of neurons 202 engaging in action potentials generate the diagnostic signal(s) 208 that are received by the monitoring electrode(s) 204. In some cases, a monitoring circuit (not illustrated) detects the diagnostic signal(s) received by the monitoring electrode(s) 204 over time. For instance, the monitoring circuit may generate data indicative of measurements of a magnitude of the diagnostic signal(s) 208 at a predetermined sampling rate.

According to some cases, the diagnostic signal(s) 208 is indicative of an activity level of the neurons 202. For instance, a distribution of the diagnostic signal(s) 208 in the frequency domain may indicate whether the neurons 202 are overactive. In particular cases, a frequency component of the diagnostic signal(s) 208 that corresponds to a frequency range above 30 Hz is indicative of an activity level of the neurons 202. For instance, if an amplitude of the frequency component of at least a portion of the diagnostic signal(s) 208 in the frequency range is above a predetermined threshold, then it may be inferred that the neurons 202 are overactive.

The overactivity of the neurons 202 may be associated with one or more pathologies. For instance, if the overactive neurons 202 are receiving reduced blood supply as a result of an ischemic stroke, then the oxygen demand of the overactive neurons 202 may exceed the supply of oxygen, thereby causing hypoxic injury to the overactive neurons 202. In some cases, the hypoxic injury results in cell death, which can cause permanent harm to a subject whose nervous system (e.g., brain) includes the overactive neurons 202. Other types of pathologies and/or negative symptoms may also be associated with neuronal activity in the brain. Examples include epilepsy, Parkinson's disease, and mental health disorders. In some cases, overactivity of the neurons 202 contributes to cell death and/or reduced neuroplasticity. Thus, in some cases, a pathology and/or negative symptom may be treated by reducing the activity of the neurons 202.

In various implementations of the present disclosure, the stimulation electrode(s) 206 is configured to output one or more treatment signals 210 to the neurons 202. For example, the treatment signal(s) 210 include at least one electrical signal output between the stimulation electrode(s) 206 and at least one reference electrode. Due to the treatment signal(s) 210, in various examples, the activity of the neurons 202 may be reduced.

In particular cases, the treatment signal(s) 210 have various characteristics associated with a reduction in neuronal activity. For example, the treatment signal(s) 210 may include pulses with a primary frequency in a range of 200 Hz to 2 kHz. The treatment signals(s) 210 may be administered in bursts that have a primary frequency in a range of 2 Hz to 10 Hz. In some cases, the treatment signal(s) 210 is administered in blocks that have a duration in a range of 10 minutes to 30 minutes.

In some implementations, one or more parameters of the treatment signal(s) 210 is altered based on the diagnostic signal(s) 208. For example, if the diagnostic signal(s) 208 indicate that overactivity in the neurons 202 is substantially reduced, then an amplitude of the treatment signal(s) 210 may be reduced, or a pause within the treatment signal(s) 210 may be extended. Thus, in some cases, the treatment signal(s) 210 may be adjusted based on the condition of the neurons 202 detected based on the diagnostic signal(s) 208.

Figure 3:
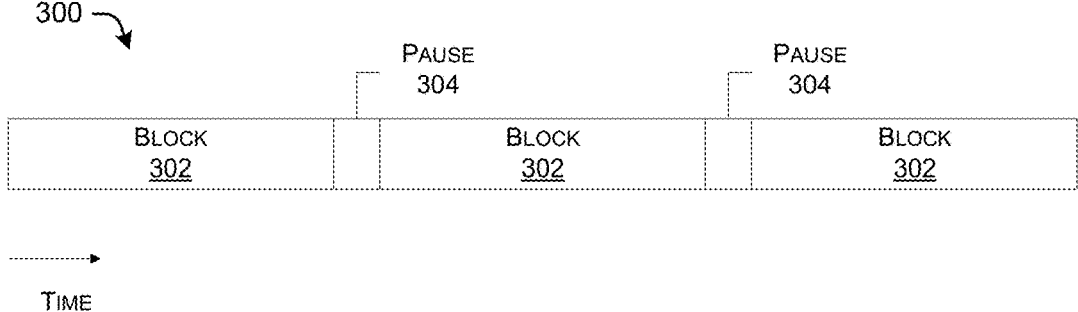
FIG. 3 illustrates an example of a treatment signal, which may be output by a stimulation electrode.

FIG. 3 illustrates an example of a treatment signal 300, which may be output by a stimulation electrode. As shown, the treatment signal 300 includes multiple blocks 302, each of which extends for the same duration. Notably, in some implementations, the blocks 302 in the treatment signal 300 may have different durations. In various examples, an individual block 302 within the treatment signal 300 has a duration that is in a range of 10 minutes to 30 minutes.

During the blocks 302, in various cases, the treatment signal 300 may include a high-frequency component (e.g., pulses) and a low-frequency component (e.g., bursts). Both the high-frequency component and the low-frequency component are configured to reduce overactivity of neurons, in various cases.

Pauses 304 occur between the blocks 302. During the pauses 304, in some cases, the treatment signal 300 is inactive. According to some implementations, an electrical signal (e.g., a diagnostic signal) is detected from the neurons during the pauses 304. An individual pause 304, in various examples, has a duration in a range of 30 seconds to five minutes.

Figure 4A:
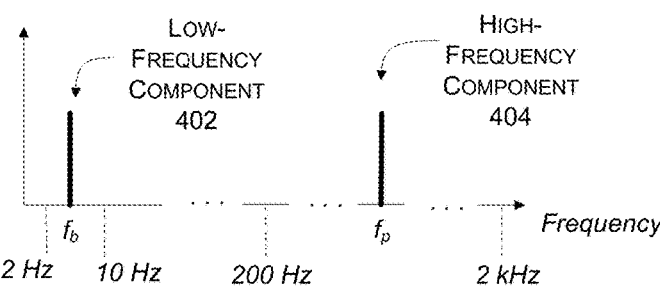
FIG. 4A illustrates a frequency domain representation of a block in a treatment signal.

FIG. 4A illustrates a frequency domain representation of a block in a treatment signal. In particular, frequency is represented on a horizontal axis and amplitude is represented on a vertical axis. In some cases, the block is administered for a predetermined duration, which may be for several minutes. For instance, the frequency domain representation illustrated in FIG. 4A can be generated by converting data indicative of a current and/or voltage of the block over time (as output by a stimulation electrode and/or as received by one or more neurons) into the frequency domain.

The block includes a low frequency-component 402 and a high-frequency component 404. The low-frequency component 402, in various cases, has a nonzero amplitude. In various examples, the low-frequency component 402 has a primary frequency $f_b$ that is within a range between 2 Hz and 10 Hz. For example, the low-frequency component 402 may represent bursts in a treatment signal. In various cases, the low-frequency component 402 is defined at additional frequencies. For instance, although not specifically illustrated in FIG. 4A, the low-frequency component 402 may represent square-wave pulses that are defined at various harmonics of the primary frequency $f_b$.

The high-frequency component 404, in various cases, also has a nonzero amplitude. The high-frequency component 404 may have a primary frequency $f_p$ that is within a range between 200 Hz and 2 kHz. For instance, the high-frequency component 404 may represent pulses in the treatment signal. In various examples, the high-frequency component 404 may have a lower amplitude than the low-frequency component 402, or may have a higher amplitude than the low-frequency component 402.

In various implementations, the low frequency component 402 is defined based on additional frequencies than $f_b$, and the high-frequency component 404 is defined based on additional frequencies than $f_p$. These additional frequencies, for instance, are not illustrated in FIG. 4A.

Figure 4B:
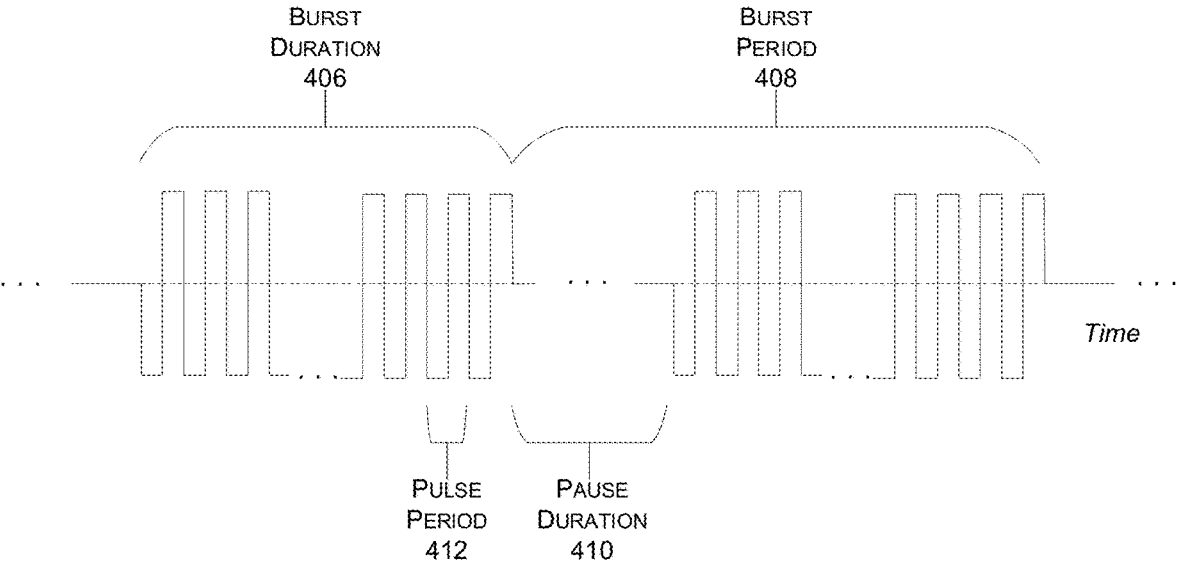
FIG. 4B illustrates an example of a time-domain version of the block described with reference to FIG. 4A.

FIG. 4B illustrates an example of a time-domain version of the block described with reference to FIG. 4A. The horizontal axis, for instance, corresponds to time and a vertical axis may represent magnitude of an electrical signal corresponding to the block.

As shown, the block includes multiple bursts having a burst duration 406 and a burst period 408. In some cases, the burst duration 406 is less than half of the burst period 408. For instance, a pause duration 410 between bursts may be longer than the burst duration 406, although implementations are not so limited. In various examples, an inverse of the burst period 408 corresponds to $f_b$.

Each burst includes multiple pulses, which have a pulse period 412. In various cases, an inverse of the pulse period 412 corresponds to $f_p$. In various implementations, the block is charge balanced.

Figure 5:
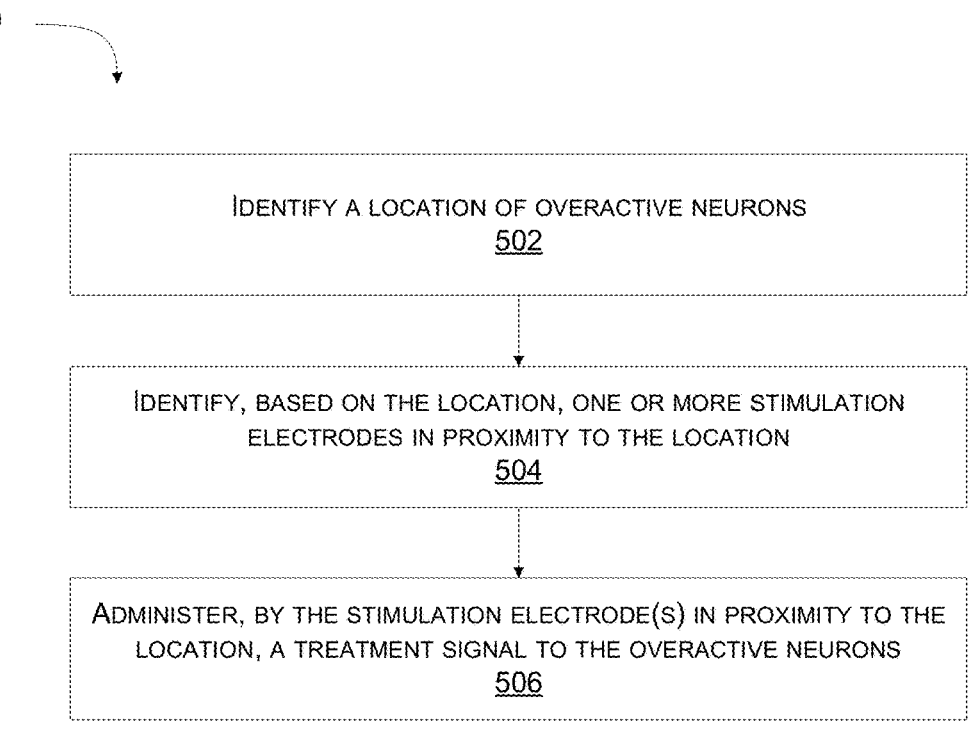
FIG. 5 illustrates an example process for treating overactive neurons using electrical stimulation.

FIG. 5 illustrates an example process 500 for treating overactive neurons using electrical stimulation. The process 500 may be performed by an entity, such as at least one processor, a computing device, a medical device, the stimulation electrodes 116, the signal generator 118, the monitoring electrodes 120, the monitoring circuit 122, the analysis system 124, or any combination thereof.

At 502, the entity identifies a location of overactive neurons. The overactive neurons, for instance, are associated with an ischemic stroke, epilepsy, Parkinson's disease, or a mental health disorder. In some cases, the entity detects a diagnostic signal from the overactive neurons, which may be a type of electrical signal. For example, the entity detects the diagnostic signal via one or more monitoring electrodes. In various cases, the entity identifies the overactive neurons based on a high-frequency portion of the diagnostic signal. For example, a frequency band defined between 30 Hz and 300 Hz is indicative of neuronal activity, and can be analyzed in order to identify neuronal overactivity. If an amplitude and/or power of a frequency component in the high-frequency portion is above a particular threshold, for instance, the entity may determine that the diagnostic signal has been received from the overactive neurons. In some cases, the entity determines the location based on the positioning of one or more monitoring electrodes that detect the diagnostic signal indicative of overactive neurons. For example, the entity may infer that the location of the overactive neurons is within a threshold distance (e.g., 1 centimeter (cm)) of the location of one or more monitoring electrodes that receive the diagnostic signal indicative of the overactive neurons. The monitoring electrodes, for instance, may include one or more ECoG electrodes, one or more EEG electrodes, or a combination thereof.

In some cases, the entity identifies the overactive neurons based on an MRI image of a brain including the overactive neurons. For example, the overactive neurons are within a brain of an individual presenting with an ischemic stroke. A blood clot, or other blockage, may at least partially occlude a blood vessel in the brain. A portion of the brain including neurons that at least partially receive blood supply from the occluded blood vessel, for instance, may engage in overactivity. The entity may identify the location of the occlusion in the brain by analyzing the MRI image. The overactive neurons, for instance, may be determined to be within a threshold distance of a portion of the blood vessel downstream of the occlusion, such as within 3 cm of the blood vessel.

At 504, the entity identifies, based on the location, one or more stimulation electrodes in proximity to the location. In various cases, the stimulation electrode(s) are within a threshold distance of the location of the overactive neurons. For example, the stimulation electrode(s) are within 10 mm of the location of the overactive neurons. In some cases, the stimulation electrode(s) are part of a broader array of stimulation electrodes that is disposed on a broader volume of the brain than the location of the overactive neurons. In some cases, the stimulation electrode(s) include one or more ECoG electrodes, one or more transcranial direct current stimulation (tDCS) electrodes, one or more transcranial alternating current stimulation (tACS) electrodes, or any combination thereof.

At 506, the entity administers, by the stimulation electrode(s) in proximity to the location, a treatment signal to the overactive neurons. In various cases, the treatment signal includes a low-frequency component. For instance, the treatment signal includes bursts having a frequency in a range of 2 Hz to 10 Hz. In some examples, the treatment signal includes a high-frequency component. For instance, the treatment signal includes pulses having a frequency in a range of 100 Hz to 2 kHz. In various implementations, the treatment signal is administered in at least one block. For instance, the block(s) have a duration in a range of 10 minutes to 30 minutes. In various implementations, the treatment signal reduces an activity level (e.g., metabolic rate, action potential firing rate, etc.) of the overactive neurons.

In various cases in which the overactive neurons are in the brain of an individual suffering an ischemic stroke, the treatment signal is administered within 24 hours of the occurrence of the ischemic stroke. For example, the treatment signal is administered within 1 hour, 2 hours, 4 hours, 6 hours, 8 hours, or 12 hours of the initial occurrence of the ischemic stroke.

Figure 6:
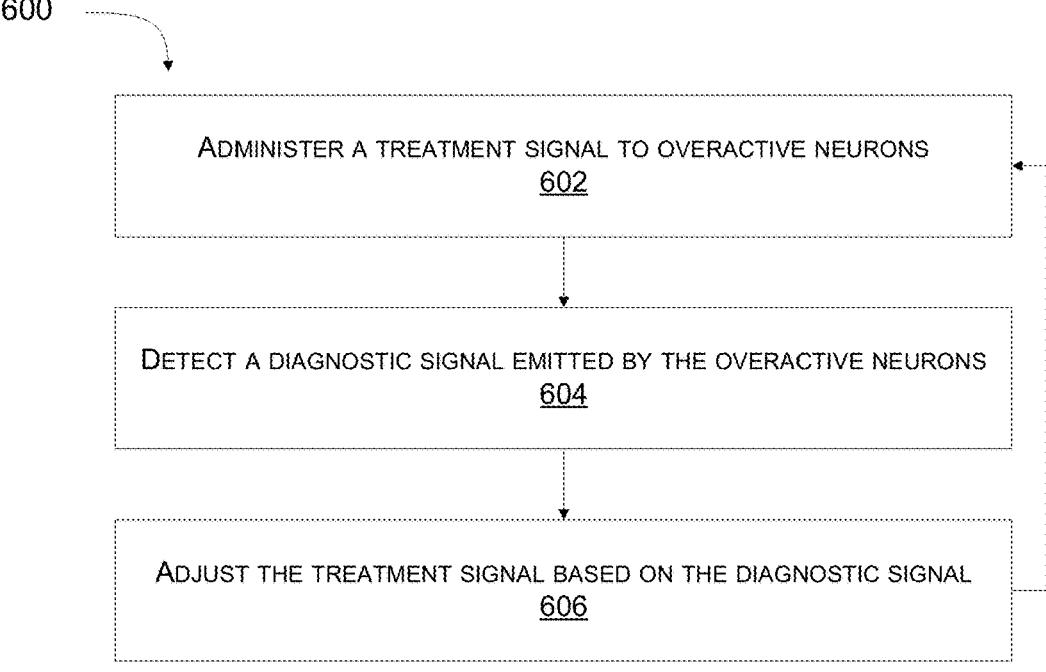
FIG. 6 illustrates an example process for adjusting an electrical stimulation treatment for overactive neurons.

FIG. 6 illustrates an example process 600 for adjusting an electrical stimulation treatment for overactive neurons. The process 600 may be performed by an entity, such as at least one processor, a computing device, a medical device, the stimulation electrodes 116, the signal generator 118, the monitoring electrodes 120, the monitoring circuit 122, the analysis system 124, or any combination thereof.

At 602, the entity may administer a treatment signal to overactive neurons. The overactive neurons, for instance, are associated with an ischemic stroke, epilepsy, Parkinson's disease, or a mental health disorder. For instance, the overactive neurons are in the brain of a subject. According to various examples, the treatment signal is output by one or more stimulation electrodes. In various cases, the stimulation electrode(s) are within a threshold distance of the location of the overactive neurons. For example, the stimulation electrode(s) are within 10 mm of the location of the overactive neurons. In some cases, the stimulation electrode(s) are part of a broader array of stimulation electrodes that is disposed on a broader volume of the brain than the location of the overactive neurons. In some cases, the stimulation electrode(s) include one or more ECoG electrodes, one or more tDCS electrodes, one or more tACS electrodes, or any combination thereof.

In various cases, the treatment signal includes a low-frequency component. For instance, the treatment signal includes bursts having a frequency in a range of 2 Hz to 10 Hz. In some examples, the treatment signal includes a high-frequency component. For instance, the treatment signal includes pulses having a frequency in a range of 100 Hz to 2 kHz. In various implementations, the treatment signal is administered in at least one block. For instance, the block(s) have a duration in a range of 10 minutes to 30 minutes. In various implementations, the treatment signal reduces an activity level (e.g., metabolic rate) of the overactive neurons.

In various cases in which the overactive neurons are in the brain of an individual suffering an ischemic stroke, the treatment signal is administered within 24 hours of the occurrence of the ischemic stroke. For example, the treatment signal is administered within 1 hour, 2 hours, 4 hours, 6 hours, 8 hours, or 12 hours of the initial occurrence of the ischemic stroke.

At 604, the entity may detect a diagnostic signal emitted by the overactive neurons. In some implementations, the diagnostic signal is defined by a voltage, a current, or other electrical signal indicative of action potentials performed by the overactive neurons being treated by the entity. In some implementations, the diagnostic signal is detected during a pause in the treatment signal. For instance, the diagnostic signal is detected between pulses and/or blocks of the treatment signal. In some cases, the diagnostic signal is detected by one or more monitoring electrodes. The monitoring electrode(s), for instance, include one or more EEG electrodes, one or more ECoG electrodes, or a combination thereof.

In various implementations, the entity analyzes the diagnostic signal. For example, the entity may convert a detected current or voltage over time to the frequency domain. In some cases, the entity performs an FFT on current or voltage measurements detected at a predetermined frequency. The entity may identify a component of the frequency domain data that corresponds to a high-frequency portion of the detected parameter. For instance, the component may be defined in a range greater than 30 Hz, such as in a range of 30 to 300 Hz. In various cases, the entity may compare an amplitude of the component to a threshold. For instance, if the amplitude is greater than the threshold, then the diagnostic signal may indicate that the overactive neurons remain overactive despite the treatment signal. However, if the amplitude is lower than the threshold, then the diagnostic signal may indicate that the overactive neurons are no longer overactive, or at least less overactive than before the treatment signal was administered.

At 606, the entity may adjust the treatment signal based on the diagnostic signal. For example, if the diagnostic signal indicates that the overactive neurons remain overactive, then the entity may retain and/or may change one or more parameters of the treatment signal to cause it to be more effective at calming overactive neurons. In various cases, if the diagnostic signal indicates that the overactive neurons are no longer overactive, then the entity may alter one or more parameters of the treatment signal that cause the treatment signal to lower its overactivity reducing effect. Example of parameters include a shape of the treatment signal, an amplitude of the treatment signal, a current of the treatment signal, a voltage of the treatment signal, a frequency of the pulses, a width of the pulses, a frequency of the bursts, a width of the bursts, a length of a pause between the bursts, a frequency of the blocks, a duration of the blocks, or a length of a pause between the blocks.

The process 600 may be performed repeatedly. For instance, the entity may readminister the treatment signal at 602 after adjusting the treatment signal at 606. In various cases, the process 600 can be performed repeatedly in order to maintain a desired level of activity in the neurons of the subject.

Figure 7:
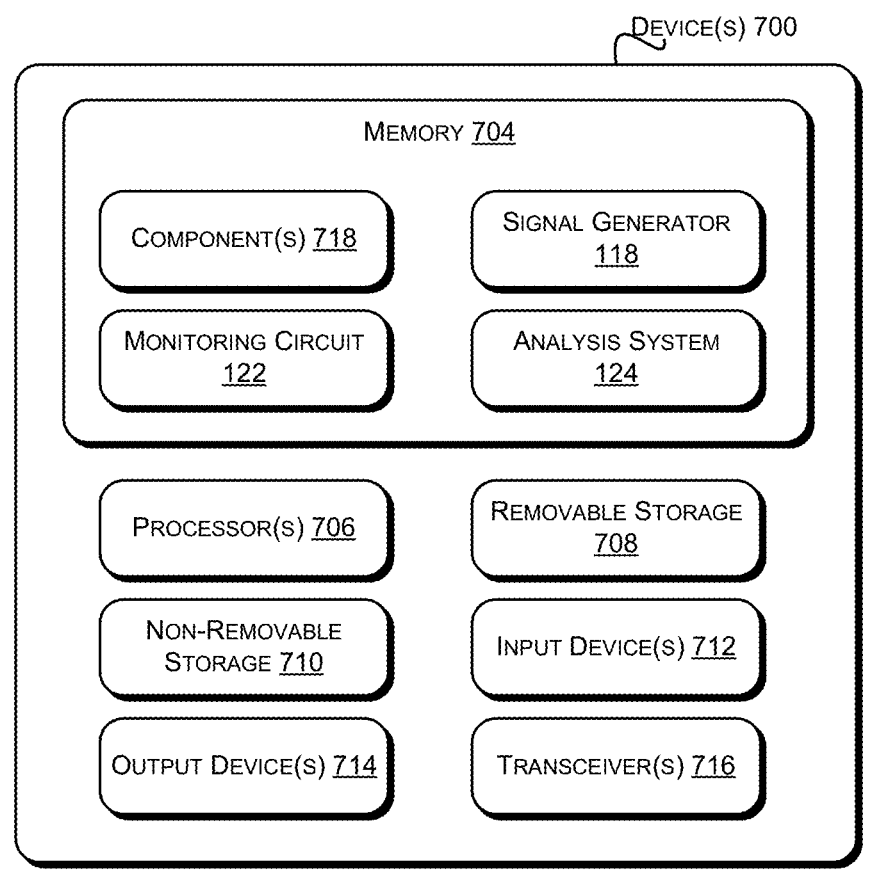
FIG. 7 illustrates an example of one or more devices that can be used to implement any of the functionality described herein.

FIG. 7 illustrates an example of one or more devices 700 that can be used to implement any of the functionality described herein. In some implementations, some or all of the functionality discussed in connection with any of the other figures described herein can be implemented in the device(s) 700. Further, the device(s) 700 can be implemented as one or more server computers 702, a network element on a dedicated hardware, as a software instance running on a dedicated hardware, or as a virtualized function instantiated on an appropriate platform, such as a cloud infrastructure, and the like. It is to be understood in the context of this disclosure that the device(s) 700 can be implemented as a single device or as a plurality of devices with components and data distributed among them.

As illustrated, the device(s) 700 include a memory 704. In various embodiments, the memory 704 is volatile (such as RAM), non-volatile (such as ROM, flash memory, etc.) or some combination of the two.

The memory 704 may store, or otherwise include, various components 706. In some cases, the components 706 can include objects, modules, and/or instructions to perform various functions disclosed herein. The components 706 can include methods, threads, processes, applications, or any other sort of executable instructions. The components 706 can include files and databases. For instance, the memory 704 may store instructions for performing operations of any of the signal generator 118, the monitoring circuit 122, or the analysis system 124.

In some implementations, at least some of the components 706 can be executed by processor(s) 708 to perform operations. In some embodiments, the processor(s) 708 includes a Central Processing Unit (CPU), a Graphics Processing Unit (GPU), or both CPU and GPU, or other processing unit or component known in the art.

The device(s) 700 can also include additional data storage devices (removable and/or non-removable) such as, for example, magnetic disks, optical disks, or tape. Such additional storage is illustrated in FIG. 7 by removable storage 710 and non-removable storage 712. Tangible computer-readable media can include volatile and nonvolatile, removable and non-removable media implemented in any method or technology for storage of information, such as computer readable instructions, data structures, program modules, or other data. The memory 704, removable storage 710, and non-removable storage 712 are all examples of computer-readable storage media. Computer-readable storage media include RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information, and which can be accessed by the device(s) 700. Any such tangible computer-readable media can be part of the device(s) 700.

The device(s) 700 also can include input device(s) 714, such as a button, keypad, a cursor control, a touch-sensitive display, voice input device (e.g., a microphone), etc. In various cases, the input device(s) 714 include one or more monitoring electrodes (e.g., the monitoring electrodes 120) and/or a medical imaging device (e.g., an MRI scanner) configured to obtain an image of a brain of a subject. The device(s) 700 may also include output device(s) 716 such as a display, speakers, printers, etc. In some implementations, the output device(s) 716 include one or more stimulation electrodes (e.g., stimulation electrodes 116). The input device(s) 714, in some cases, may include a device configured to detect input signals from a user (e.g., a clinician), such an input signal causing the device(s) 700 to initiate or to conclude a treatment.

As illustrated in FIG. 7, the device(s) 700 can also include one or more wired or wireless transceiver(s) 716. For example, the transceiver(s) 716 can include a Network Interface Card (NIC), a network adapter, a Local Area Network (LAN) adapter, or a physical, virtual, or logical address to connect to the various base stations or networks contemplated herein, for example, or the various user devices and servers. The transceiver(s) 716 can include any sort of wireless transceivers capable of engaging in wireless, Radio Frequency (RF) communication. The transceiver(s) 716 can also include other wireless modems, such as a modem for engaging in Wi-Fi, WiMAX, Bluetooth, or infrared communication.

Experimental Example: Neuroprotective Effects of Electrical Stimulation Following Ischemic Stroke in Non-Human Primates Brain stimulation is a novel therapy for ischemic stroke, a major cause of brain injury that often results in lifelong disability. Previous in vitro and rodent studies have reported the impact of stimulation after stroke (Lay, et al. PLOS ONE, vol. 5, no. 6, p. e11270, June 2010; Notturno et al., J. Neurol. Sci., vol. 342, no. 1, pp. 146-151, July 2014; Peruzzotti-Jametti et al., Stroke, vol. 44, no. 11, pp. 3166-3174, November 2013; Wang, et al., Front. Aging Neurosci., vol. 13, 2021; Buetefisch, et al., Ann. Neurol., vol. 93, no. 2, pp. 336-47, 2023). However, these results have not been replicated in humans due to significant scale and anatomical differences, in addition to a limited understanding of stimulation-induced network changes.

This Example combines electrophysiology and histology to study the effects of electrical stimulation following cortical ischemic stroke in non-human primates (NHPs). To produce controlled focal lesions, we used the photothrombotic method to induce targeted vasculature damage in the sensorimotor cortices of two macaques while collecting ECoG signals bilaterally. In another two macaques, we followed the same lesioning procedures and applied repeated electrical stimulation via an ECoG electrode medial to the lesion. The protective effects of stimulation on neural dynamics was investigated using a variety of electrophysiological markers such as ECoG signal power and coherence. In addition, histological analysis, including Nissl and immunohistochemistry staining, was performed to evaluate the differences in lesion volume, neuronal death, and neuroinflammatory response.

Brain plasticity has been widely observed during behavioral tasks and recovery after damage. Brain stimulation can take advantage of this plasticity to serve as a potential therapy for ischemic stroke, a major cause of brain injury that results in lifelong disability. Therefore, electrophysiology and histology were also combined to study the mechanisms of neuroplasticity following ischemic stroke and electrical stimulation in NHPs.

In comparison to controls, the ECoG signals described in this Example showed decreased gamma power across the sensorimotor cortex in stimulated animals. Meanwhile, histology revealed smaller lesion volumes for the stimulated group, suggesting that electrical stimulation may exert neuroprotection by suppressing post-ischemic neural activity and reducing excitotoxicity. With the similarity between NHP and human brains, this study indicates that similar forms of electrical stimulation may also produce beneficial effects in human brains.

This study utilizes a novel set of approaches investigating electrical stimulation-induced neuroprotection. A lesion-based toolbox was combined with state-of-the-art neurophysiology techniques to study the neuroprotective effects of electrical stimulation following acute ischemic stroke in NHPs. Multiple aspects of stimulation-induced network changes from large areas (~3 cm$^2$ per hemisphere) of the macaque sensorimotor cortex were compared at 0-4 hours after stroke. The insights gained from these experiments inform the development of next-generation electrical stimulation paradigms that can be used as an alternative treatment to minimize neuronal damage, promote functional recovery, and reduce severe disabilities for stroke patients.

Methods

Animals and Surgical Procedures

All animal procedures were approved by the University of Washington Institutional Animal Care and Use Committee. Surgeries were conducted through the Tissue Distribution Program at the Washington National Primate Research Center (WaNPRC), which aims to conserve and fully utilize the NHPs no longer needed for other experiments. Using standard aseptic technique, 4 adult rhesus macaques (Control group: monkey D, female, 12.8 kg, 14 years; monkey E, female, 13.10 kg, 14 years; Stim group: monkey F, female, 13.8 kg, 14 years; monkey G, male, 14.6 kg, 7 years) were anesthetized with isoflurane and placed in a stereotaxic frame. The animal's temperature, oxygen saturation, heart rate, and electrocardiographic responses were monitored throughout the procedure. Bilateral craniotomies and durotomies were performed using stereotaxic coordinates that target the sensorimotor cortices. A semi-transparent multi-modal artificial dura containing 32 ECoG electrodes (described in Griggs, et al., J. Neural Eng., vol. 18, no. 5, p. 055006, April 2021) was implanted bilaterally on top of the cortical surface in each cranial window for subsequent electrophysiology recording and electrical stimulation.

Induction of Focal Ischemic Lesions

Figures 8, 9:
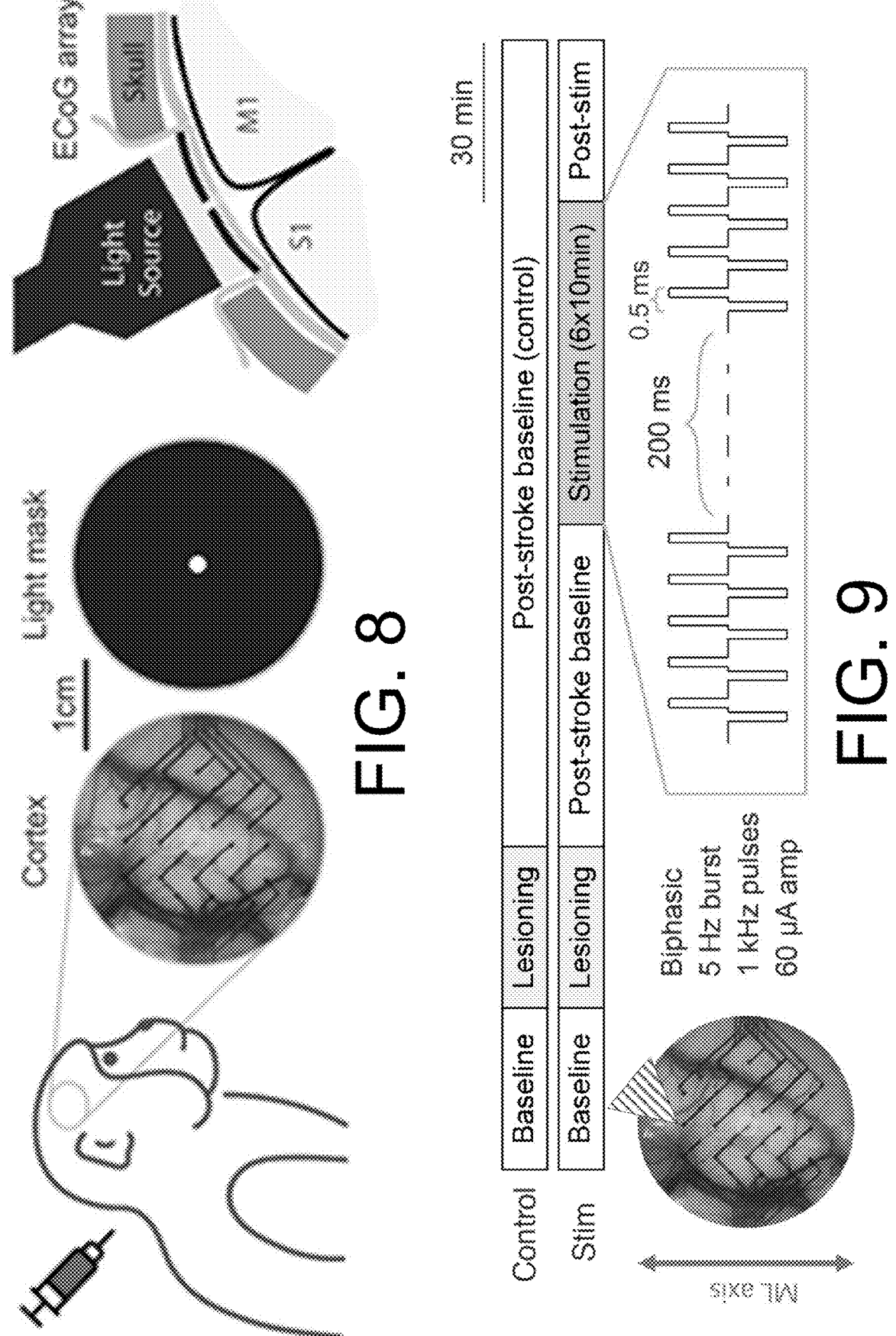
FIG. 8 illustrates a diagram showing an example process and apparatus for inducing focal ischemic lesions.
FIG. 9 illustrates an example of electrical signals administered to subject non-human primates (NHPs) and monitoring time periods.

FIG. 8 illustrates a diagram showing the process and apparatus for inducing focal ischemic lesions, as used in this Experimental Example. A previously developed method for creating ischemic lesions in NHPs based on the photothrombotic technique (described in Khateeb et al., 2019 41st Annual International Conference of the IEEE Engineering in Medicine and Biology Society (EMBC), July 2019, pp. 3515-3518; Labat-gest and Tomasi, J. Vis. Exp. JoVE, no. 76, p. 50370, June 2013) was performed, which produces focal infarct by photo-activation of a light-sensitive dye (Rose Bengal). Upon illumination, the intravenously administered dye produced singlet oxygen that damaged endothelial cell membranes, causing platelet aggregation and interrupting local blood flow. In this experiment, 30 minutes of baseline recording with the ECoG electrodes was performed and then a unilateral infarct in the sensorimotor cortex of each of the 4 monkeys was induced with a consistent location. This was achieved by illuminating the ipsilesional cranial window for 30 minutes through a 1.5-mm diameter aperture using an uncollimated white light source after Rose Bengal injection (FIG. 1A). Simultaneous electrophysiology recording was performed to monitor the extent of neuronal damage and network dynamics around the site of injury as the lesion was forming and up to 4 hours post-illumination.

Electrophysiology Recording and Electrical Stimulation

FIG. 9 illustrates an example of electrical signals administered to subject NHPs and monitoring time periods. Electrophysiology recording and electrical stimulation were performed with two Grapevine Nomad processors and four Nano front ends (Ripple Neuro, Salt Lake City, UT). In all monkeys, ECoG data was collected bilaterally for ~4 hours at a 30 kHz sampling frequency. In monkeys F and G, electrical stimulation was performed and delivered through a single ECoG electrode at ~8 mm medially from the lesion center on the ipsilesional (left) hemisphere (FIG. 9, arrow). The stimulation trains in 6 blocks lasted 10 minutes each, with 2 minutes of baseline recordings in between the blocks to track changes in neurophysiology as stimulation continues. The stimulation trains had a 5 Hz burst frequency and 5 biphasic charge-balanced pulses at 1 kHz within each burst. The stimulation amplitude was 60 μA and the pulse width was 200 μs per phase with 50 μs inter-phase interval. Other previous studies report similar stimulation parameters (Cogan, J. Neural Eng., vol. 13, no. 2, p. 021001, January 2016; Rebesco and Miller, J. Neural Eng., vol. 8, no. 1, p. 016011, February 2011).

Electrophysiology Data Analysis

The raw 30 kHz signals were down-sampled to 1 kHz and filtered into distinct frequency bands including delta (1-4 Hz), theta (4-7 Hz) and gamma (30-59 Hz). The signal power was then calculated over multiple time windows, including pre-stroke baseline, post-stroke, during-stimulation, and post-stimulation, at each electrode for the frequency bands defined above.

Next, the functional connectivity changes between electrodes within either the lesion region or the corresponding area in the contralesional cortex were analyzed by their pairwise coherence. This magnitude-squared coherence ($C_{xy}$) between signals at electrodes x and y was computed as a function of the respective power spectral densities of signals x and y ($P_{xx}$ and $P_{yy}$) and their cross-spectral density ($P_{xy}$) using 10 s Hamming windows across every 2 minutes of data.

Histological Analysis

At ~4 hours after the stroke is induced, animals were deeply sedated and transcardially perfused with phosphate buffered saline (PBS) and followed by 4% paraformaldehyde (PFA). The brains were harvested and post-fixed by immersion in 4% PFA for 24 to 48 hours. A coronal block containing the lesioned region was dissected using a custom matrix and then stored at 4° C. in 30% sucrose in PBS. For staining, the block was frozen and sectioned into 50 μm thick coronal sections using a sliding microtome (Leica). Sliced sections were stored at 4° C. in PBS with 0.02% sodium azide. To evaluate the extent of ischemic damage and neuronal death, Nissl staining was performed on mounted coronal sections surrounding the lesion with ~0.45 mm separation between sections using Thionin acetate. Nissl-stained slices were then scanned and registered in MATLAB (2019b, MathWorks) for three-dimensional (3D) reconstruction and estimation of lesion volumes. The registered images were then smoothed, binarized, and went through edge detection so that infarct boundaries on each slice could be identified for 3D visualization. The widths and depths from representative coronal slices of each lesion were also calculated based on image resolution.

Results

Figure 10:
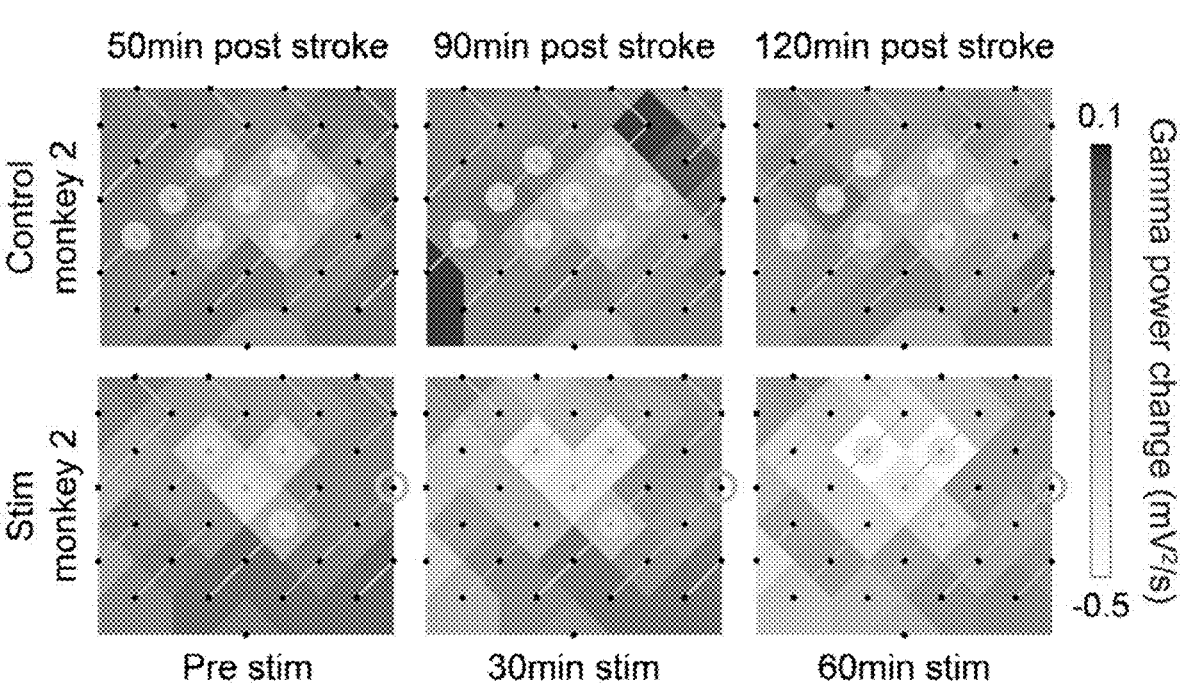
FIG. 10 illustrates heatmaps of gamma neuronal activity over time for an example control subject and an example stimulated subject.

FIG. 10 illustrates heatmaps of neuronal activity over time for an example control subject an example stimulated subject. For instance, "control" NHP subjects did not receive an electrical stimulation treatment post-ischemic stroke, whereas "stimulated" NHP subjects did receive the electrical stimulation treatment post-ischemic stroke. The large-scale ECoG recordings were analyzed to monitor the sensorimotor neural activity and the acute physiological changes driven by the ischemic lesion and electrical stimulation were characterized. As shown in FIG. 10, the gamma power change in the stimulated subject (bottom row) is significantly lower than the gamma power change in the control subject. In the gamma frequency band, distinctively low power was detected at electrodes closest to the previously illuminated region (center of the array) during post-stroke periods in both control and stimulated monkeys. This observation confirmed the localized neuronal damage caused by photothrombosis. Interestingly, a gradual, large-scale downregulation of high frequency gamma activity was also observed across the entire ipsilesional sensorimotor region in response to post-stroke stimulation for monkeys in the stimulation group. This was distinctively different from what was observed in the control group where gamma power at some of the perilesional electrodes was elevated at 30 minutes post the stimulation start time. These results suggest that gamma power was selectively suppressed over large areas as stimulation continued, reflecting reduced neuronal activity level in response to post-stroke stimulation.

Figure 11:
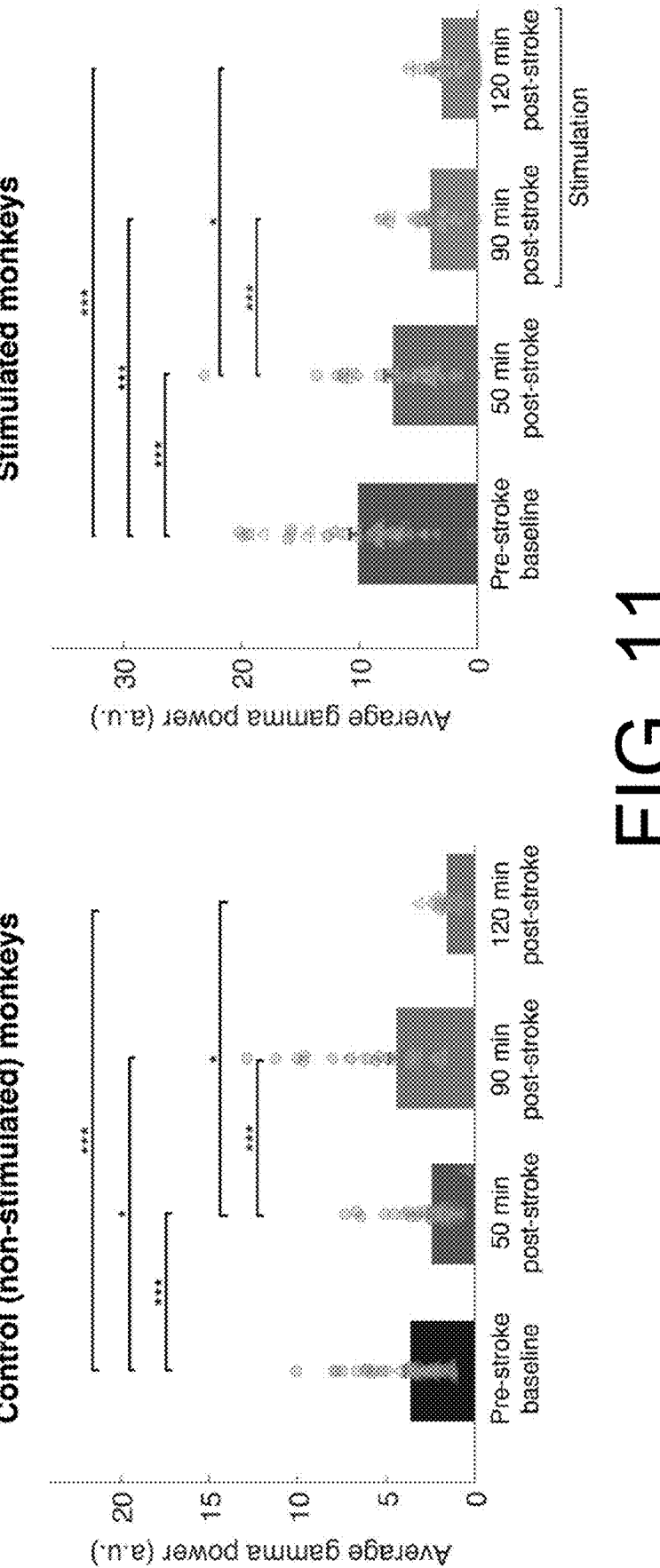
FIG. 11 illustrates average gamma power in the control and stimulated subjects over time.

FIG. 11 illustrates average gamma power in the control and stimulated subjects over time. FIG. 11 also illustrates that the stimulated subjects have significantly reduced average gamma power after 120 minutes post-stroke, when compared to the control subjects.

Figure 12:
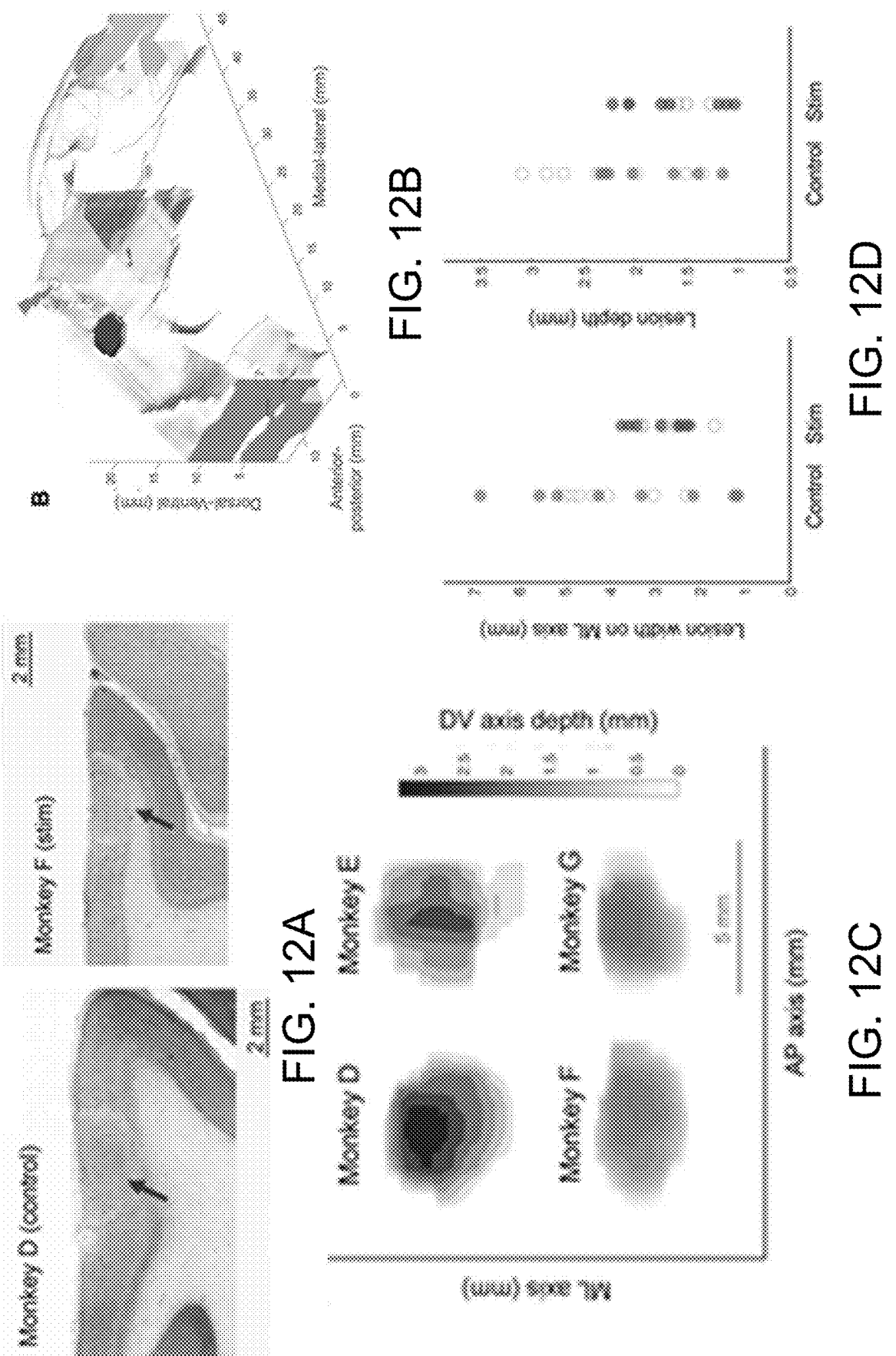
FIGS. 12A to 12D illustrate example results of assessing cell death and lesion volumes.

FIGS. 12A to 12D illustrate results of assessing cell death and lesion volumes. To confirm the extent of cell death and estimated lesion volumes in control and stimulation animals, Nissl staining was performed using fixed coronal sections. The loss of Nissl substance inside ischemic cores led to distinct pale areas and well-defined boundaries on the stained sections (FIG. 12A). Using this identified lesion boundary and linear interpolation, the lesions were reconstructed in 3D space (FIG. 12B) and their volumes were estimated in each animal. In control monkeys D and E, the estimated lesion volumes were 35.3 and 28.4 mm$^3$ respectively, while in the stimulated monkeys F and G, the lesion volumes were 20.3 and 15.9 mm$^3$ respectively, smaller than the controls on both the medial-lateral (ML) and dorsal-ventral (DV) axes (FIG. 12C-D). Note that the stimulation pulses were also delivered medially from the lesion center. Together, these results suggest that the downregulation of gamma activity observed in FIGS. 10 to 12D was not caused by additional neuronal death in the stimulated region, and that monkeys receiving post-stroke electrical stimulation showed smaller infarction at around 4 hours after ischemic lesioning.

Figure 13:
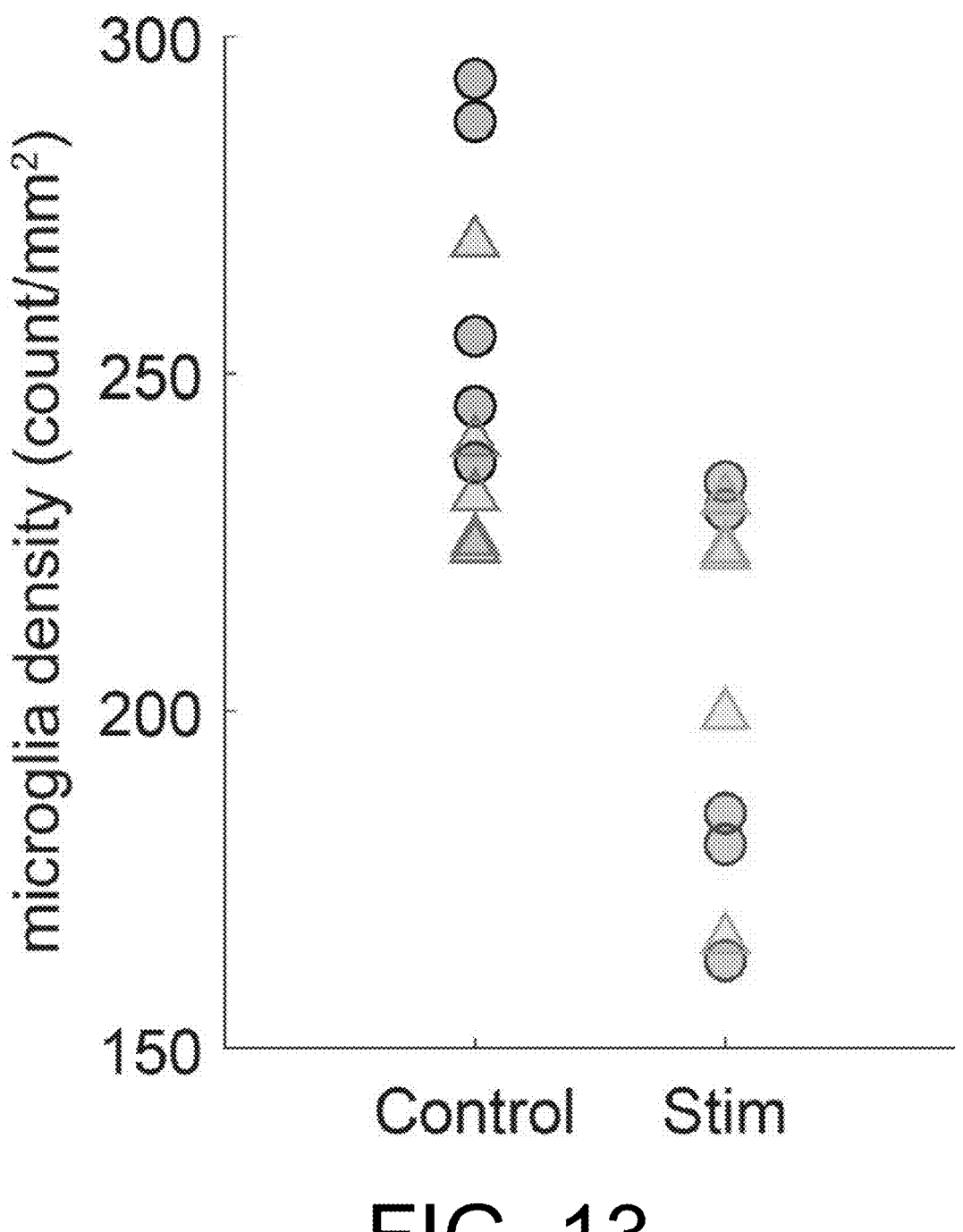
FIG. 13 illustrates example microglia density for control subjects and stimulation subjects.

FIG. 13 illustrates microglia density for the control subjects and the stimulation subjects. In various cases, ischemia-induced neuroinflammation can be assessed based on microglia migration (e.g., density) in a particular volume. As shown in FIG. 13, there was higher observed microglia density near the lesion boundary in the control subjects.

Discussion

In this study, the photothrombotic method was used to produce focal ischemic lesions in NHP subjects. In comparison to other interventions for generating infarcts in NHPs, this method is less surgically challenging and allows for more reliable control the location and size of infarcts across animals by implementing the same aperture, intensity, and duration of light illumination. Controlled focal lesions were generated in the sensorimotor region of NHPs using this method, while simultaneously collecting ECoG recordings from the impacted brain to monitor neural activity changes. For the lesion volume estimation and electrophysiology analysis, results from control monkeys D and E were compared to results from stimulated monkeys F and G, which were lesioned using identical illumination parameters that have shown to induce predictable infarct sizes (K. Khateeb et al., Cell Rep. Methods, vol. 2, no. 3, p. 100183, March 2022). However, for monkey E, extensive loss of NeuN-positive cells, but normal density of Nissl-stained cells over the top layers of the exposed sensorimotor cortex, were observed. Monkey C was added as an additional control and monkey E was excluded for immunohistochemistry procedures. Monkey C received lower intensity of illumination through various apertures, and thus had multiple smaller lesions to serve as no-stimulation controls for the immunohistochemistry analysis, while helping to distinguish the effect of electrical stimulation from natural variabilities of photothrombotic infarct sizes.

Repeated electrical stimulation was applied adjacent to the lesion on the ipsilesional cortex, 60 minutes after lesion induction in monkeys F and G. The stimulation train contained 5 Hz bursts of biphasic pulses, similar to the theta burst stimulation (TBS) pattern of transcranial magnetic stimulation (TMS) protocols that are widely adopted in the clinic (Huang, et al., Neuron, vol. 45, no. 2, pp. 201-206, January 2005). In past studies, continuous TBS protocols have been reported to have an inhibitory effect on synaptic transmission and cortical excitability in human subjects (Huang, et al., Clin. Neurophysiol., vol. 122, no. 5, pp. 1011-18, May 2011; Stagg et al., "J. Neurophysiol., vol. 101, no. 6, pp. 2872-2877, June 2009). The stimulation paradigm of this Example used five pulses at 1 kHz in each burst comparing to the three 50-100 Hz pulses in a traditional TBS protocol. Stimulation via high frequency pulses at greater than ~200 Hz have been shown to have an inhibitory effect on neuronal firing rates (Yazdan-Shahmorad, et al., Brain Stimulat., vol. 4, no. 4, pp. 228-241, October 2011). Meanwhile, similar patterns of pulse train have also been used for paired-pulse conditioning through intracortical microstimulation and were shown to promote Hebbian-like plasticity in rodents (Rebesco and Miller, J. Neural Eng., vol. 8, no. 1, p. 016011, February 2011). Given that the ECoG recordings obtained for this Example showed decreasing gamma power over the course of stimulation but not in control animals, and that gamma activity in ECoG has been shown to correlate with neuronal firing (Yazdan-Shahmorad, et al., J. Neural Eng., vol. 10, no. 6, p. 066002, October 2013), applying theta bursts of electrical stimulation over the sensorimotor cortex may have decreased neuronal activation and network excitability through mechanisms similar to those seen in continuous TBS and high frequency pulse trains which induce hyperpolarization and synaptic depression (Huang, et al., Clin. Neurophysiol., vol. 122, no. 5, pp. 1011-18, May 2011; Beurrier, et al., J. Neurophysiol., vol. 85, no. 4, pp. 1351-56, April 2001). As smaller infarct volume was observed in the stimulated animals along with the down-regulated neural activity, the results provide evidence that cortical stimulation prevents tissue damage by reducing excessive depolarization and glutamate-mediated excitotoxicity adjacent to the lesion during the ischemic cascades. This neuroprotective mechanism is supported by the therapeutic strategies of pharmacological agents designed for acute ischemic stroke, which aims to attenuate excitotoxicity and restore the balance between oxygen supply and energy consumption by inhibiting neuronal excitability (Cheng et al., "Neuroprotection for ischemic stroke: Two decades of success and failure," vol. 1, no. 1, p. 10, 2004; Chamorro, et al., Lancet Neurol., vol. 15, no. 8, pp. 869-81, July 2016).

Immunohistochemistry staining was performed against c-Fos and Iba1 to assess neuronal activation and microglial response in the perilesional tissues of the control and stimulated animals. The reduced density of both c-Fos and Iba1 positive cells around the lesion boundary provided complimentary information in addition to the electrophysiology results above, suggesting that electrical stimulation reduced both the level of cortical depolarization and neuroinflammation for tissues going through the acute ischemic pathway. These results confirmed what has been reported before for rodents receiving cortical stimulation via bipolar electrodes (Wang, et al., "Somatosensory Cortical Electrical Stimulation After Reperfusion Attenuates Ischemia/Reperfusion Injury of Rat Brain," Front. Aging Neurosci., vol. 13, 2021; Baba, et al., Stroke, vol. 40, no. 11, pp. e598-e605, November 2009) or cathodal transcranial direct current stimulation (C-tDCS) (Notturno, et al. J. Neurol. Sci., vol.

342, no. 1, pp. 146-151, July 2014; Peruzzotti-Jametti, et al., *Stroke, vol.* 44, no. 11, pp. 3166-74, November 2013), in which stimulation decreased tissue damage by inhibiting apoptosis, neuroinflammation, and peri-infarct depolarization during acute stroke. In addition, the decrease in c-Fos immunoreactivity in the stimulated monkeys suggests that the downregulation of ECoG activity is not a manifestation of cortical spreading depression (which can be harmful), since an upregulation of c-Fos has been shown to correlate with sustained depolarizations and the subsequent spreading depression in the presence of focal ischemia (Hermann, et al., Neuroscience, vol. 104, no. 4, pp. 947-55, July 2001). Combined with the reduction in both lesion size and microglial accumulation, the results suggest that electrical stimulation applied one hour after stroke onset offered inhibitory and protective effects instead of exacerbating tissue damage attributed to spreading depolarization as previously described for early sensory stimulation (von Bornstädt et al., *Neuron*, vol. 85, no. 5, pp. 1117-31, March 2015), making this stimulation protocol a safe treatment option for acute ischemic stroke.

This study reveals possible mechanisms of stimulation-induced neuroprotective effects after acute ischemic stroke by combining the latest technology in electrophysiology and histology with a unique NHP stroke model. The results indicate that early electrical stimulation may decrease the extent of neuronal cell death by reducing peri-infarct depolarization, excitotoxicity, and inflammation in the sensorimotor cortex of NHPs. These findings suggest that using perilesional electrical stimulation to protect the brain and reduce tissue damage during acute ischemic stroke could play a role in alleviating the global burden of stroke, as infarct size is a major determining factor of mortality and the functional outcome of chronic stroke rehabilitation strategies.

CONCLUSION

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof.

This document cites to various printed publications, articles, journals, patent documents, and other references. Each one of the references described is incorporated by reference herein in its entirety.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of $\pm 20\%$ of the stated value; $\pm 19\%$ of the stated value; $\pm 18\%$ of the stated value; $\pm 17\%$ of the stated value; $\pm 16\%$ of the stated value; $\pm 15\%$ of the stated value; $\pm 14\%$ of the stated value; $\pm 13\%$ of the stated value; $\pm 12\%$ of the stated value; $\pm 11\%$ of the stated value; $\pm 10\%$ of the stated value; $\pm 9\%$ of the stated value; $\pm 8\%$ of the stated value; $\pm 7\%$ of the stated value; $\pm 6\%$ of the stated value; $\pm 5\%$ of the stated value; $\pm 4\%$ of the stated value; $\pm 3\%$ of the stated value; $\pm 2\%$ of the stated value; or $\pm 1\%$ of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

The invention claimed is:
1. A medical device for treating acute ischemic stroke, the medical device comprising:

an array of electrocorticography (ECoG) electrodes configured to be disposed on a surface of a brain and comprising:

at least one monitoring electrode configured to detect, from overactive neurons in the brain, a first electrical signal having a frequency component in a range between 30 Hz and 400 Hz with an amplitude that is above a predetermined threshold; and at least one stimulation electrode configured to output a treatment signal configured to reduce an activity of the overactive neurons;

a monitoring circuit coupled to the at least one monitoring electrode and configured to receive signals from the at least one monitoring electrode to detect overactive neurons in the brain, wherein the overactive neurons emit a first electrical signal having a frequency component in a range between 30 Hz and 400 Hz with an amplitude that is above a predetermined threshold; and a signal generator coupled to the at least one stimulation electrode and configured to cause the at least one stimulation electrode to output a treatment signal configured to reduce an activity of the overactive neurons by outputting, to the at least one stimulation electrode, a second electrical signal that is charge balanced and comprises:

a low-frequency component comprising bursts having a frequency in a range of about 2 Hertz (Hz) to about 10 Hz;

a high-frequency component comprising pulses having a frequency in a range of about 200 Hz to about 2 kilohertz (kHz); and one or more blocks having a duration in a range of about 10 minutes to about 30 minutes.

2. The medical device of claim 1, further comprising:

a processor configured to:

determine, by analyzing the first electrical signal, a location of a portion of the brain comprising the overactive neurons, the overactive neurons being overactivated by the ischemic stroke in an acute phase, the portion of the brain comprising the overactive neurons bordering a portion of neurons blocked from receiving oxygenated blood by at least one blockage in at least one blood vessel;

identify the at least one stimulation electrode, among the array, within a distance in a range of about 0.5 millimeters (mm) to about 10 mm of the location of the portion of the brain; and based on identifying the at least one stimulation electrode, cause the signal generator to output the second electrical signal to the at least one stimulation electrode.

3. The medical device of claim 1, wherein the treatment signal is configured to reduce the activity of the overactive neurons by reducing an action potential rate of the overactive neurons.

4. The medical device of claim 1, further comprising:

a processor configured to:

identify, by analyzing an MRI image of the brain, a location of an occluded blood vessel in the brain;

determine a location of a portion of the brain that is within a threshold distance of the location of the occluded blood vessel downstream of an occlusion in the occluded blood vessel, the portion of the brain comprising the overactive neurons;

identify the at least one stimulation electrode, among the array, within a distance in a range of about 0.5 millimeters (mm) to about 10 mm of the location of the portion of the brain; and based on identifying the at least one stimulation electrode, cause the signal generator to output the second electrical signal to the at least one stimulation electrode.

5. A medical device, comprising:

at least one monitoring electrode;

a monitoring circuit coupled to the at least one monitoring electrode and configured to identify, from signals received from the at least one monitoring electrode, a group of neurons exhibiting overactivity, the group of neurons emitting a first electrical signal having a frequency component in a range between 30 Hz and 400 Hz with an amplitude that is above a predetermined threshold;

at least one stimulation electrode configured to:

output a treatment signal configured to reduce an activity of a group of neurons in a brain, the group of neurons outputting a first electrical signal having a frequency component in a range between 30 Hz and 400 Hz with an amplitude that is above a predetermined threshold; and to be disposed away from the group of neurons exhibiting overactivity by a distance in a range of about 0.5 mm to 3 centimeters (cm); and a signal generator coupled to the at least one stimulation electrode and configured to output, to cause the at least one stimulation electrode, a to output the treatment signal by outputting a second electrical signal to the at least one stimulation electrode, the second electrical signal comprising:

a low-frequency component comprising bursts having a frequency in a range of about 2 Hertz (Hz) to about 10 Hz; and a high-frequency component comprising pulses having a frequency in a range of about 200 Hz to about 2 kilohertz (KHz).

6. The medical device of claim 5, wherein the at least one stimulation electrode comprises at least one of one or more ECoG electrodes, one or more transcranial direct current stimulation (tDCS) electrodes, or one or more transcranial alternating current stimulation (tACS) electrodes.

7. The medical device of claim 5, wherein the group of neurons comprise overactive neurons.

8. The medical device of claim 7, wherein the overactive neurons are in a brain of a subject experiencing at least one of an ischemic stroke, epilepsy, Parkinson's disease, or a mental health disorder.

9. The medical device of claim 7, wherein the overactive neurons are supplied with blood from a blood vessel that is at least partially occluded.

10. The medical device of claim 5, wherein the second electrical signal further comprises one or more blocks having a duration in a range of about 10 minutes to about 30 minutes.

11. The medical device of claim 5, further comprising:

at least one monitoring electrode configured to detect the first electrical signal from the group of neurons; and at least one processor configured to:

identify, based on the first electrical signal, a portion of a brain comprising the group of neurons; and based on identifying the portion of the brain comprising the group of neurons, cause the signal generator to output the second at least one electrical signal.

12. The medical device of claim 11, wherein the at least one processor is configured to identify the portion of the brain comprising the group of neurons further based on a magnetic resonance imaging (MRI) image.

13. The medical device of claim 11, wherein the at least one monitoring electrode comprises at least one ECoG electrode and/or at least one EEG electrode.

14. A method, comprising:

identifying a portion of a brain comprising overactive neurons outputting a first electrical signal having a frequency component in a range between 30 Hz and 400 Hz with an amplitude that is above a predetermined threshold; and reducing an activity of the overactive neurons by outputting, to at least one stimulation electrode disposed away from the portion of the brain by a distance in a range of about 0.5 mm to 1 centimeter (cm), a second electrical signal comprising:

a low-frequency component comprising bursts having a frequency in a range of about 2 Hertz (Hz) to about 10 Hz; and a high-frequency component comprising pulses having a frequency in a range of about 200 Hz to about 2 kilohertz (kHz).

15. The method of claim 14, wherein identifying the portion of the brain comprising the overactive neurons comprises:

identifying data indicative of neuronal activity of the brain; and identifying the portion of the brain by analyzing the data.

16. The method of claim 15, wherein the data indicative of neuronal activity of the brain comprises at least one of a magnetic resonance imaging (MRI) image or the first electrical signal emitted from at least one of the overactive neurons.

17. The method of claim 14, the second electrical signal further comprising:

one or more blocks having a duration in a range of about 10 minutes to about 30 minutes.

18. The method of claim 14, the electrical signal being a first electrical signal, the method further comprising:

detecting, from at least one of the overactive neurons, the first electrical signal; and based on the first electrical signal:

modifying at least one parameter of the second electrical signal; or selecting the at least one stimulation electrode among an array of electrodes.

19. The method of claim 18, wherein the at least one parameter comprises at least one of a shape of the second electrical signal, an amplitude of the second electrical signal, a current of the second electrical signal, a voltage of the second electrical signal, a frequency of the pulses, a width of the pulses, a frequency of the bursts, a width of the bursts, a length of a pause between the bursts, or a time at which the second electrical signal is output to the at least one stimulation electrode.

20. The method of claim 14, wherein reducing the activity of the overactive neurons comprises reducing an action potential rate of the overactive neurons until a clot in an occluded blood vessel in the brain is removed.

* * * * *